US007666905B2

(12) United States Patent
Pace-Asciak

(10) Patent No.: US 7,666,905 B2
(45) Date of Patent: Feb. 23, 2010

(54) COMPOSITIONS COMPRISING HEPOXILIN ANALOGS AND THEIR USE IN THE TREATMENT OF CANCER

(76) Inventor: Cecil Pace-Asciak, Suite 5270, 555 University Avenue, Toronto, Ontario (CA) M5G 1X8

( * ) Notice: Subject to any disclaimer, the term of this patent is extended or adjusted under 35 U.S.C. 154(b) by 0 days.

(21) Appl. No.: 10/999,195

(22) Filed: Nov. 29, 2004

(65) Prior Publication Data

US 2005/0272671 A1 Dec. 8, 2005

Related U.S. Application Data

(63) Continuation of application No. PCT/CA03/00780, filed on May 28, 2003.

(60) Provisional application No. 60/383,134, filed on May 28, 2002.

(51) Int. Cl.
| | |
|---|---|
| A61K 31/336 | (2006.01) |
| A61K 31/38 | (2006.01) |
| A61K 31/396 | (2006.01) |
| A61K 31/201 | (2006.01) |
| A61K 31/202 | (2006.01) |
| C07D 203/08 | (2006.01) |
| C07D 331/02 | (2006.01) |
| C07D 303/14 | (2006.01) |
| C07D 303/18 | (2006.01) |
| C07D 303/12 | (2006.01) |
| C07D 303/04 | (2006.01) |

(52) U.S. Cl. .................. 514/475; 514/430; 514/183; 514/559; 514/560; 548/968; 549/90; 549/561

(58) Field of Classification Search .............. 514/560, 514/430
See application file for complete search history.

(56) References Cited

U.S. PATENT DOCUMENTS

| 5,616,607 | A | | 4/1997 | Pace-Asciak et al. |
|---|---|---|---|---|
| 6,093,741 | A | * | 7/2000 | Gosselin et al. .............. 514/560 |
| 6,391,305 | B1 | * | 5/2002 | Feng et al. ............... 424/193.1 |

FOREIGN PATENT DOCUMENTS

| WO | WO9729751 | 8/1997 |
|---|---|---|
| WO | WO9959578 | 11/1999 |
| WO | WO0110422 | 2/2001 |
| WO | WO0238157 | 5/2002 |

OTHER PUBLICATIONS

Pace-Asciak et. al. Current Pharmaceutical Design, 2006, 12, 963-969.*
Goodman & Gilman's: The Pharmacological Basis of Therapeutics, 10th Edition, McGraw-Hill Medical Publishing Division, 2001, pp. 54-56.*
Sawyers et. al. J. Clin. Onco. 19(18), 2001, 13s-16s.*
Merck Manual of Diagnostics,17th Edition, 1999, pp. 973-995.*
Arndt et al., "Liposomal Bleomycin: Increased Therapeutic Activity and Decreased Pulmonary Toxicity in Mice" Drug Delivery (2001) vol. 8, pp. 1-7.*
Mauro et al, (2002), "STI571: A Paradigm of New Agents for Cancer Therapeutics", *J. Clin. Oncol.*, V. 20, pp. 325-334.
Seppa, N., (2001), "Leukemia Overpowers Drug in Two Ways", *Science News*, V. 159, p. 389.
Rajaratnam et al, (2001), "Imatinib for Chronic Myelogenous Leukemia: A Nice Mess", *Lancet*, V. 358, p. 1902.
O'Brian, S.G., (2001), "Imatinib for Chronic Myelogenous Leukemia: A Nice Mess", *Lancet*, pp. 1902-1903.
Lim et al, (2001), "Imatinib for Chronic Myelogenous Leukemia: A Nice Mess", *Lancet*, V. 358, p. 1903.
Cheng, G.S., (2000), "Dramatic Results in Trial of New Leukemia Drug", *Family Practice News*, Feb. 1, 2000, v. 10, p. 1.
Jankov et al, (2002), "Hepoxilin Analogs Inhibit Bleomycin-Induced Pulmonary Fibrosis in the Mouse" *J.P.E.T.*, V. 301, pp. 435-440.
Weisberg et al (2000), "Mechanism of Resistance to the ABL Tyrosine Kinase Inhibitor ST1571 in BCR/ABL-transformed hematopoietic cell lines", *Blood*, V. 95, pp. 3498-3505.

* cited by examiner

*Primary Examiner*—Shaojia Anna Jiang
*Assistant Examiner*—Eric S Olson
(74) *Attorney, Agent, or Firm*—Dinsmore & Shohl LLP

(57) ABSTRACT

Methods and pharmaceutical compositions comprise at least one hepoxilin analog of the formula (I)

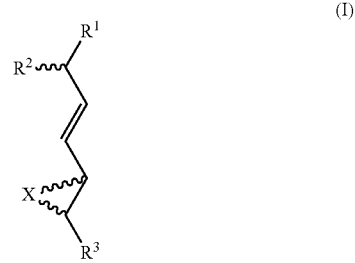

wherein X and $R^3$ are as defined herein. The methods are directed to treatment of a cancer and for promotion of a apoptosis in a cancer cell.

15 Claims, 12 Drawing Sheets

COMPOSITIONS COMPRISING HEPOXILIN ANALOGS AND THEIR USE IN THE TREATMENT OF CANCER

RELATED APPLICATIONS

The present application is a continuation under 35 U.S.C. §120 of PCT/CA03/00780 filed May 28, 2003, which claims priority under 35 U.S.C. §119 of U.S. application Ser. No. 60/383,134 filed May 28, 2002.

FIELD OF THE INVENTION

The invention relates to methods and pharmaceutical compositions for treating cancers, particularly leukemias.

BACKGROUND OF THE INVENTION

Leukemia is the name applied to a group of related cancers which arise from the bone marrow and other blood-producing organs.

The cancerous cells reproduce rapidly, suppressing the production of 1) normal white cells that are essential to fighting infection in the body, 2) red cells needed to carry oxygen in the blood, and 3) platelets needed in the coagulation of blood. The uncontrolled proliferation of the stem cells in the bone marrow affects the production of the essential mature cells. Cancer cells may spread to the liver, spleen, lymph nodes, genitals or the brain (Tran, 1995).

Two forms of leukemia exist, the acute form which is of sudden onset and rapid progression, commonly found in children, and the chronic form, which progresses slowly with few symptoms for many years (even up to 20 years). A large proportion of acute or childhood leukemia (50-70%) is now curable since the advance of therapeutic strategies involving chemoactive drugs, radiation and bone marrow transfusion techniques (Tran, 1995).

Chronic leukemia is a disease of too many mature white cells (Cherath, 1995). Unlike acute leukemia, in which the process of maturation of the stem cell precursors is interrupted, in chronic leukemia the cells are still able to mature but, although appearing normal, they do not function as mature cells, but multiply slowly and in an unregulated way. They survive much longer than normal white cells and build up in the body. Two types of chronic leukemia exist. Chronic lymphocytic leukemia (CLL) involves the B and T lymphocytes, with abnormalities of the former being more common. In chronic myelogenous leukemia (CML), the cells affected are the granulocytes.

CML is a serious disease, still with a poor prognosis. Some 32% of newly diagnosed patients will survive 5 years (Cherath, 1995). The drug STI-571 (known also as Gleevac and Imatinib)(Mauro et al., 2002; Seppa, 2001; Lim and Muir, 2001; Rajaratnam and Edwards, 2001; O'Brien, 2001) created considerable hope for patients with advanced CML, as it appeared to reduce significantly elevated white cell counts. Unfortunately, leukemia cells develop resistance to the drug as treatment continues and the disease recurs. There therefore remains a need for improved treatments for CML.

The hepoxilins are biologically active metabolites of arachidonic acid formed through the 12(S)-lipoxygenase pathway. Four natural hepoxilins have been identified, the A-type hepoxilins consisting of two epimers having a hydroxyl group at carbon 8 (8(S, R)-hydroxy-11(S), 12(S)-epoxy-eicosa-5Z, 9E, 14Z-trienoic acid) and the B-type, two epimers having a hydroxyl group at carbon 10 (10(S,R)-hydroxy-11(S), 12(S)-epoxy-eicosa-5Z, 8Z, 14Z-trienoic acid).

A number of hepoxilin analogs have been described which, along with the native hepoxilins, exhibit a variety of pharmacological effects, including raising intracellular calcium, inhibiting thromboxane formation and action (International Patent Application WO 02/38157), stimulation of insulin release (International Patent Application WO 01/10422) and lowering of blood glucose.

It has not, however, previously been shown or suspected that hepoxilin analogs would be effective to control the growth of cancerous cells.

SUMMARY OF THE INVENTION

New methods and pharmaceutical compositions are provided for treating cancer in mammals. The hepoxilin analogues described herein appear to act by restoring or promoting apostosis in cancer cells. These analogues may be used to restore or promote the normal apoptotic process in cancers in mammals. These compounds are non-toxic and well tolerated in mammals and are as effective, and in some cases more effective, than some presently clinically approved drugs for cancer treatment.

In accordance with one embodiment, the invention provides a method for treating a cancer in a mammal comprising administering to the mammal an effective amount of at least one hepoxilin analog of the formula:

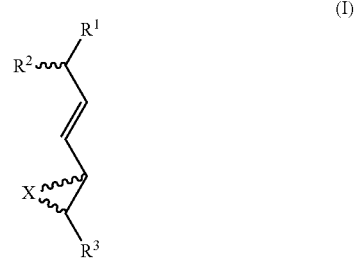
(I)

wherein X is S, NH or $C_nH_{2n}$ where n is 1 to 4;

$R^1$ is lower alkyl or alkenyl;
  lower alcohol (C1 to C22), saturated or unsaturated;
  —$CH_2CH=CH$—$(CH_2)_3$—COR" wherein R" is OH, O— lower alkyl or alkenyl; or
  Y—$R^4$ wherein
  Y is —$CH_2$—CH=CH—$(CH_2)_3$, lower alkyl or alkenyl and
  $R^4$ is CONH-Z or COO-Z wherein
  Z is a sugar moiety;

$R^2$ is OH, $NH_2$, SH, $OPO_3H$, lower alkyl or alkenyl or O— lower alkyl or alkenyl; and $R^3$ is lower alkyl or alkenyl or
  —$CH_2$—CH=CH—$(CH_2)_4$—R''' wherein R''' is $CH_3$, $CH_2OH$, $CH_2$—O— lower alkyl or alkenyl, phenyl or substituted phenyl

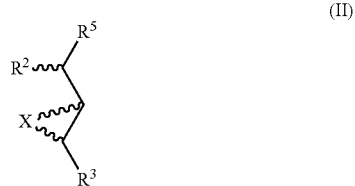
(II)

wherein X, $R^2$ and $R^3$ are as defined for formula I and
$R^5$ is lower alkyl or alkenyl;
  lower alcohol (C1 to C22), saturated or unsaturated;
  —CH=CH—$CH_2$—CH=CH—$(CH_2)_3$—COR''
  wherein R''=OH or O— lower alkyl or alkenyl; or
  Y—$R^6$ wherein
  Y is —CH=CH—$CH_2$—CH=CH—$(CH_2)_3$, lower alkyl or alkenyl and
  $R^6$ is CONH-Z or COO-Z wherein
  Z is a sugar moiety.

In accordance with a further embodiment, the invention provides a pharmaceutical composition comprising at least one hepoxilin analog of the formula:

(I)

wherein X is S, NH or $C_nH_{2n}$ where n is 1 to 4;
$R^1$ is lower alkyl or alkenyl;
  lower alcohol (C1 to C22), saturated or unsaturated;
  —$CH_2$CH=CH—$(CH_2)_3$—COR'' wherein R'' is OH, O— lower alkyl or alkenyl; or
  Y—$R^4$ wherein
  Y is —$CH_2$—CH=CH—$(CH_2)_3$, lower alkyl or alkenyl and
  $R^4$ is CONH-Z or COO-Z wherein
  Z is a sugar moiety;
$R^2$ is OH, $NH_2$, SH, $OPO_3H$, lower alkyl or alkenyl or O— lower alkyl or alkenyl; and
$R^3$ is lower alkyl or alkenyl or
  —$CH_2$—CH=CH—$(CH_2)_4$—R''' wherein R''' is $CH_3$, $CH_2OH$, $CH_2$—O— lower alkyl or alkenyl, phenyl or substituted phenyl

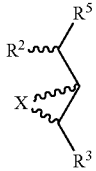

(II)

wherein X, $R^2$ and $R^3$ are as defined for formula I and
$R^5$ is lower alkyl or alkenyl;
  lower alcohol (C1 to C22), saturated or unsaturated; or
  —CH=CH—$CH_2$—CH=CH—$(CH_2)_3$—COR''
  wherein R''=OH or O— lower alkyl or alkenyl; or
  Y—$R^6$ wherein
  Y is —CH=CH—$CH_2$—CH=CH—$(CH_2)_3$, lower alkyl or alkenyl and
  $R^6$ is CONH-Z or COO-Z wherein
  Z is a sugar moiety
and a pharmaceutically acceptable carrier.

In accordance with a further embodiment, the invention provides the use of at least one hepoxilin analog of the formula:

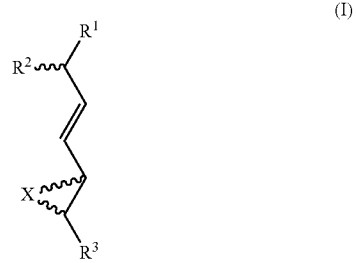

(I)

wherein X is S, NH or $C_nH_{2n}$ where n is 1 to 4;
$R^1$ is lower alkyl or alkenyl;
  lower alcohol (C1 to C22), saturated or unsaturated;
  —$CH_2$CH=CH—$(CH_2)_3$—COR'' wherein R'' is OH, O— lower
  alkyl or alkenyl; or
  Y—$R^4$ wherein
  Y is —$CH_2$—CH=CH—$(CH_2)_3$, lower alkyl or alkenyl and
  $R^4$ is CONH-Z or COO-Z wherein
  Z is a sugar moiety;
$R^2$ is OH, $NH_2$, SH, $OPO_3H$, lower alkyl or alkenyl or O— lower alkyl or alkenyl; and
$R^3$ is lower alkyl or alkenyl or
  —$CH_2$—CH=CH—$(CH_2)_4$—R''' wherein R''' is $CH_3$, $CH_2OH$, $CH_2$—O— lower alkyl or alkenyl, phenyl or substituted phenyl

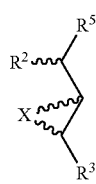

(II)

wherein X, $R^2$ and $R^3$ are as defined for formula I and
$R^5$ is lower alkyl or alkenyl;
  lower alcohol (C1 to C22), saturated or unsaturated; or
  —CH=CH—$CH_2$—CH=CH—$(CH_2)_3$—COR''
  wherein R''=OH or O— lower alkyl or alkenyl; or
  Y—$R^6$ wherein
  Y is —CH=CH—$CH_2$—CH=CH—$(CH_2)_3$, lower alkyl or alkenyl and
  $R^6$ is CONH-Z or COO-Z wherein
  Z is a sugar moiety in the preparation of a medicament for the treatment of cancer.

In accordance with a further embodiment, the invention provides the use of at least one hepoxilin analog of the formula:

(I)

wherein X is S, NH or $C_nH_{2n}$ where n is 1 to 4;
$R^1$ is lower alkyl or alkenyl;
  lower alcohol (C1 to C22), saturated or unsaturated;
  —$CH_2CH$=$CH$—$(CH_2)_3$—COR" wherein R" is OH, O— lower alkyl or alkenyl; or
  Y—$R^4$ wherein
  Y is —$CH_2$—$CH$=$CH$—$(CH_2)_3$, lower alkyl or alkenyl and
  $R^4$ is CONH-Z or COO-Z wherein
  Z is a sugar moiety;
$R^2$ is OH, $NH_2$, SH, $OPO_3H$, lower alkyl or alkenyl or O— lower alkyl or alkenyl; and
$R^3$ is lower alkyl or alkenyl or —$CH_2$—$CH$=$CH$—$(CH_2)_4$—R'" wherein R'" is $CH_3$, $CH_2OH$, $CH_2$—O— lower alkyl oralkenyl, phenyl or substituted phenyl or

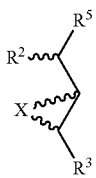

(II)

wherein X, $R^2$ and $R^3$ are as defined for formula I and
$R^5$ is lower alkyl or alkenyl;
  lower alcohol (C1 to C22), saturated or unsaturated; or
  —CH=CH—$CH_2$—CH=CH—$(CH_2)_3$—COR"
  wherein R"=OH or O— lower alkyl or alkenyl; or
  Y—$R^6$ wherein
  Y is —CH=CH—$CH_2$—CH=CH—$(CH_2)_3$, lower alkyl or alkenyl and
  $R^6$ is CONH-Z or COO-Z wherein
  Z is a sugar moiety for the treatment of cancer.

In accordance with a further embodiment, the invention provides a method for promoting apoptosis or restoring normal apoptosis in a cancer cell comprising administering to the cell an effective amount of at least one hepoxilin analog of the formula:

(I)

wherein X is S, NH or $C_nH_{2n}$ where n is 1 to 4;
$R^1$ is lower alkyl or alkenyl;
  lower alcohol (C1 to C22), saturated or unsaturated;
  —$CH_2CH$=$CH$—$(CH_2)_3$—COR" wherein R" is OH, O— lower alkyl or alkenyl; or
  Y—$R^4$ wherein
  Y is —$CH_2$—$CH$=$CH$—$(CH_2)_3$, lower alkyl or alkenyl and
  $R^4$ is CONH-Z or COO-Z wherein
  Z is a sugar moiety;
$R^2$ is OH, $NH_2$, SH, $OPO_3H$, lower alkyl or alkenyl or O— lower alkyl or alkenyl; and
$R^3$ is lower alkyl or alkenyl or
  —$CH_2$—$CH$=$CH$—$(CH_2)_4$—R'" wherein R'" is $CH_3$, $CH_2OH$, $CH_2$—O— lower alkyl or alkenyl, phenyl or substituted phenyl or

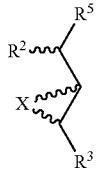

(II)

wherein X, $R^2$ and $R^3$ are as defined for formula I and
$R^5$ is lower alkyl or alkenyl;
  lower alcohol (C1 to C22), saturated or unsaturated; or
  —CH=CH—$CH_2$—CH=CH—$(CH_2)_3$—COR"
  wherein R"=OH or O— lower alkyl or alkenyl; or
  Y—$R^6$ wherein
  Y is —CH=CH—$CH_2$—CH=CH—$(CH_2)_3$, lower alkyl or alkenyl and
  $R^6$ is CONH-Z or COO-Z wherein
  Z is a sugar moiety.

In accordance with a further embodiment, the invention provides a method for screening a candidate compound for its ability to inhibit cancer cell growth comprising determining the effect of the compound on cytochrome c release or caspase-3 activation.

SUMMARY OF DRAWINGS

Certain embodiments of the invention are described, reference being made to the accompanying drawings, wherein:

FIG. 5, Panel B, shows photomicrographs of K562 cells treated with the indicated compounds and stained with Hoechst 33342 dye to show nuclear fragmentation.

DETAILED DESCRIPTION OF THE INVENTION

Figure 1:
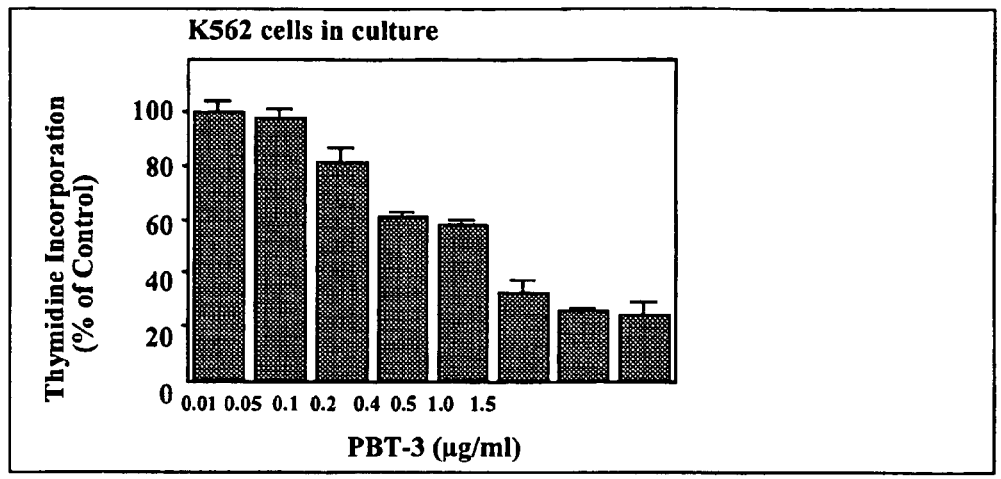
FIG. 1 shows the effect of various doses of the hepoxilin methyl ester PBT-3 on $^3$H-thymidine incorporation in K562 CML cells.

The present invention provides methods and pharmaceutical compositions for treating cancer in a subject in need of such treatment.

It has been shown that hepoxilin analogs are potent inhibitors of leukemia cell growth and act to promote apoptosis of leukemia cells. Apoptosis is the process of natural or programmed cell death by which normal cells are disposed of when they are no longer needed. Cancer cells have escaped from this normal control and do not undergo apoptosis, but go on to proliferate in an unregulated fashion.

The hepoxilin analogs appear to act by restoring or promoting the apoptotic process in cancer cells. The treatment methods and pharmaceutical compositions described herein are therefore applicable to any type of cancer in which one wishes to restore or promote apoptosis.

Cancers which may be treated by the methods and pharmaceutical compositions of the invention include carcinomas, adenocarcinomas, sarcomas, lymphomas and leukemias, cancers of the brain, bladder, prostate, breast, liver, spleen, lung, gut and other organs and tissues.

The hepoxilin analogs described herein may be used preferably to treat the group of cancers known as leukemia, including acute or chronic lymphocytic leukemia and acute or chronic myelogenous leukemia.

In the hepoxilin analogs employed in the methods and compositions of the invention, the epoxide at position C11-C12 of the native hepoxilins is replaced by another group, such as S, NH or $C_nH_{2n}$ where n is 1 to 4.

Hepoxilin analogs which may be used in the methods of the invention include compounds of the formula:

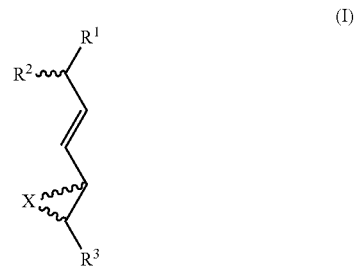

(I)

wherein X is S, NH or $C_nH_{2n}$ where n is 1 to 4;
$R^1$ is lower alkyl or alkenyl;
  lower alcohol (C1 to C22), saturated or unsaturated;
  —$CH_2CH$=$CH$—$(CH_2)_3$—$COR''$ wherein R" is OH, O— lower alkyl or alkenyl; or
  Y—$R^4$ wherein
  Y is —$CH_2$—$CH$=$CH$—$(CH_2)_3$, lower alkyl or alkenyl and
  $R^4$ is CONH-Z or COO-Z wherein
  Z is a sugar moiety;
$R^2$ is OH, $NH_2$, SH, $OPO_3H$, lower alkyl or alkenyl or O— lower alkyl or alkenyl; and
$R^3$ is lower alkyl or alkenyl or
  —$CH_2$—$CH$=$CH$—$(CH_2)_4$—$R'''$ wherein R'" is $CH_3$, $CH_2OH$, $CH_2$—O— lower alkyl or alkenyl, phenyl or substituted phenyl or

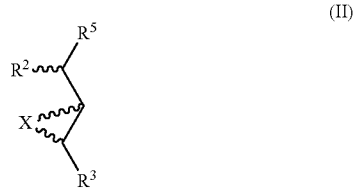

(II)

wherein X, $R^2$ and $R^3$ are as defined for formula I and
$R^5$ is lower alkyl or alkenyl;
  lower alcohol (C1 to C22), saturated or unsaturated;
  —$CH$=$CH$—$CH_2$—$CH$=$CH$—$(CH_2)_3$—$COR''$
  wherein R"=OH or O— lower alkyl or alkenyl; or
  Y—$R^6$ wherein
  Y is —$CH$=$CH$—$CH_2$—$CH$=$CH$—$(CH_2)_3$, lower alkyl or alkenyl and $R^6$ is CONH-Z or COO-Z wherein
Z is a sugar moiety.

As used herein, "alkyl" and "alkenyl" mean branched or unbranched alkyl or alkenyl radicals. "Lower alkyl or alkenyl" means C1 to C22 alkyl or alkenyl.

As used herein, "a sugar moiety" means a monosaccharide, a disaccharide or a polysaccharide. Suitable monosaccharides include, for example, glucose, fructose, galactose and ribose. Suitable disaccharides include, for example, sucrose, maltose and lactose.

Substituted phenyl includes phenyl substituted with —OH, I, Br, Cl or lower alkyl or alkenyl.

Sugar amide and sugar ester derivatives of the native hepoxilins analogous to the hepoxilin analog sugar amide and ester derivatives depicted above may also be used in the methods and compositions of the invention.

The sugar moiety may be linked to the hepoxilin at any position of the sugar ring which can form an amide or ester bond.

One group of preferred hepoxilin analogs are:

PBT-1 which is 8(S) hydroxy-11, 12-cyclopropyl-eicosa-5Z, 9E14Z-trienoic acid methyl ester, and the corresponding trienoic free acid;

PBT-2 which is 8(R)-hydroxy-11, 12-cyclopropyl-eicosa-5Z, 9E, 14Z-trienoic acid methyl ester, and the corresponding trienoic free acid; PBT-2 which is 8(R)-hydroxy-1 1, 12-cyclopropyl-eicosa-5Z, 1-0E9E, 14Z-trienoic acid acid methyl ester, and the corresponding trienoic free acid;

PBT-3 which is 10(S)-hydroxy-11,12-cyclopropyl-eicosa-5Z,8Z,14Z-trienoic acid methyl ester, and the corresponding trienoic free acid; and PBT-4 which is 10(R)-hydroxy-11,12-cyclopropyl-eicosa-5Z,8Z,14Z-trienoic acid methyl ester, and the corresponding trienoic free acid.

These analogs and their preparation are described in U.S. Pat. No. 5,616,607, the contents of which are incorporated herein by reference.

A further preferred group of hepoxilin analogs which may be used in the methods of the invention are water-soluble derivatives of the hepoxilins such as sugar amides and sugar esters.

Preferred hepoxilin analog sugar amide derivatives are:
1-(2-deoxy-2-amidogalactopyranosyl)-8(S)-hydroxy-11,12-cyclopropyl-eicosa-5Z,9E,14Z-trienamide (PBT-10);
1-(2-deoxy-2-amidogalactopyranosyl)-8(R)-hydroxy-11,12-cyclopropyl-eicosa-5Z,9E,14Z-trienamide (PBT-20);
1-(2-deoxy-2-amidogalactopyranosyl)-10(S)-hydroxy-11, 12-cyclopropyl-eicosa-5Z,8Z,14Z-trienamide (PBT-30); and
1-(2-deoxy-2-amidogalactopyranosyl)-10(R)-hydroxy-11, 12-cyclopropyl-eicosa-5Z,8Z,14Z-trienamide (PBT-40).

Preferred hepoxilin analog sugar ester derivatives are:
1-(6-galactopyranosyl)-8(S)-hydroxy-11,12-cyclopropyl-eicosa-5Z,9E,14Z-trienoate (PBT-100);
1-(6-galactopyranosyl)-8(R)-hydroxy-11,12-cyclopropyl-eicosa-5Z,9E,14Z-trienoate (PBT-200);
1-(6-galactopyranosyl)-10(S)-hydroxy-11,12-cyclopropyl-eicosa-5Z,8Z,14Z-trienoate (PBT-300); and
1-(6-galactopyranosyl)-10(R)-hydroxy-11,12-cyclopropyl-eicosa-5Z,8Z,14Z-trienoate (PBT-400).

The sugar amide and sugar ester derivatives of hepoxilin analogs described herein have improved water-solubility compared with other derivatives of these hepoxilin analogs, thus providing compounds with greater bioavailability in vivo.

The sugar amide and sugar ester hepoxilin analogs of the invention can be synthesised, for example, as described in International Patent Application No. WO 02/38157, the contents of which are incorporated herein by reference. The first step is the synthesis of the corresponding hepoxilin analog methyl ester as described in U.S. Pat. No. 5,616,607, the contents of which are incorporated herein by reference. The methyl ester is hydrolysed to give the free acid by conventional methods, followed by formation of the N-hydroxy succinimide ester as described in WO 02/38157. The succinimide ester is then converted to a sugar amide, also as described in WO 02/38157.

The sugar ester hepoxilin analogs of the invention can also be synthesised by the following method. The 8(10) hydroxy group in the methyl ester of hepoxilin is protected by treatment with tert-butyldimethylchlorosilane followed by hydrolysis of the methyl ester group as described in WO 02/38157. The obtained 8(10) protected free acid is coupled by carbodiimide method with tetra-protected sugar and then deprotected, as further described in WO 02/38157.

The hepoxilin analogs described herein have been shown to give effective control of cancer cell growth, providing lasting cell kill with no demonstrable remaining cancer cells which are able to survive. These compounds are as effective as, and in some cases more effective than, the clinically proven drug STI571.

Hepoxilin analogs may be administered to a subject in need of treatment either alone or in combination with one or more other anti-cancer chemotherapeutic compounds. Especially useful is the combination of a hepoxilin analog with another anti-cancer compound which acts by a different mechanism. This may provide a treatment which is less likely to lead to drug resistance of the cancer cells.

For example, the apoptotic effect of the drug STI-571 involves binding of the compound to the protein, Bcr-Abl tyrosine kinase, on CML cells, thereby disabling them. Bcr-Abl phosphorylates Crkl, which in turn binds to the kinase and links it to other proteins in a signaling pathway that triggers white blood cells to proliferate. Relapse appears to be related to an alteration in the Bcr-Abl gene which mutates further to encode a modified Bcr-Abl tyrosine kinase that is unresponsive to STI-571, preventing STI-571 from binding to it (Cheng 2000; Seppa, 2001).

Another pathway involved in apoptosis is the lipid-activated PKB/Akt pathway. Its upstream regulators are important transducers of phosphoinositol 3-kinase (PI3K)-derived signaling for this and related serine/threonine kinases which control transcription and protein translation involved in the regulation of cell growth, survival and metabolism. PKB/Akt kinases are G-protein coupled, requiring phosphorylation at threonine 308 for activity.

The Akt pathway has been implicated in several pathological processes, such as inflammation, diabetes and cancer. The pivotal role of this pathway in malignancy has been well defined and extensively documented. The PI3-K/Akt signalling pathway is overactive in many major cancer types and controls such processes as angiogenesis, apoptosis, cell migration and proliferation. Thus, cancers with up-regulated PI3-K/Akt activity are highly aggressive, often metastasize, and become resistant to conventional therapy. As shown herein, Akt phosphorylation is blocked by hepoxilin analogs such as PBT-3 leading to a decrease in proliferation and induction of apoptosis. Hepoxilin analogs may therefore be used in combination with STI-571 to treat leukemia by interacting with both the Akt and Bcl pathways respectively.

PBT-3 has been shown to be as effective as STI571 in inducing apoptosis in K562 cells. The hepoxilin analog appears to stimulate apoptosis by releasing cytochrome c and activating caspase-3.

In accordance with a further embodiment, the invention provides methods for screening candidate compounds for their ability to inhibit growth of cancer cells and to stimulate apoptosis of cancer cells by examining their effect on cytochrome c release and/or caspase-3 activation in assay systems such as those described herein.

In a further embodiment, a method for screening a candidate compound for its ability to inhibit growth of cancer cells comprises treating a culture of cancer cells such as those described herein with the candidate compound and comparing the activity of the candidate compound with the activity of one of the hepoxilin analogs described herein in the same assay.

The invention further includes anti-cancer compounds identified by these screening methods.

The hepoxilin analogs described herein are known from previous studies to be non-toxic and well tolerated in mammals, at doses up to 40 mg/kg (Jankov, 2002). Their safety is further confirmed by the studies described herein, where no effect of the compounds on apoptosis was seen in normal muscle, adipocyte and bone marrow cells.

The analogs have been shown to be bioavailable after both oral and intra-peritoneal administration (Jankov, 2002).

In accordance with the methods and compositions of the present invention, one or more hepoxilin analogs may be administered to a mammal in a variety of forms depending on the selected route of administration, optionally along with a pharmaceutically acceptable carrier, as will be understood by those skilled in the art. The compositions of the invention may be administered orally, intraperitoneally or parenterally, the latter route including intravenous and subcutaneous administration. Parenteral administration may be by continuous infusion over a selected period of time. The compositions may also be administered directly into a solid tumour or closely adjacent to a solid tumour, so as to be carried by the tumour vasculature into the tumour. Forms for injectable use include sterile aqueous solutions or dispersion and sterile powders for the extemporaneous preparation of sterile injectable solutions or dispersions. In all cases the form must be sterile and must be fluid to the extent that easy syringability exists.

The hepoxilin analog may be orally administered with an inert diluent or with an assimilable edible carrier, or it may be enclosed in hard or soft shell gelatin capsules, compressed into tablets or incorporated directly with the food of the diet. For oral therapeutic administration, a hepoxilin analog may be incorporated with excipient and used in the form in ingestible tablets, buccal tablets, troches, capsules, elixirs, suspensions, syrups, wafers and the like.

Compositions containing one or more hepoxilin analogs can also be administered orally or intravenously in a solution or emulsion contained within phospholipid vesicles called liposomes. The liposomes may be unilamellar or multilamellar and are formed of constituents selected from phosphatidylcholine, dipalmitoylphosphatidylcholine, cholesterol, phosphatidylethanolamine, phosphatidylserine, dimyristoylphosphatidylcholine and combinations thereof. The multilamellar liposomes comprise multilamellar vesicles of similar composition to unilamellar vesicles, but are prepared so as to result in a plurality of compartments in which the analogs containing solution or emulsion is entrapped. Additionally, other adjuvants and modifiers may be included in the liposomal formulation such as polyethyleneglycol, or other materials.

The liposomes containing the hepoxilin or hepoxilin analog compositions may also have modifications such as having antibodies immobilized on the surface of the liposome in order to target their delivery.

Pharmaceutical compositions containing one or more hepoxilin analogs may be administered to any living organism in need of anti-cancer treatment in a safe and effective amount. By safe and effective, as used herein, is meant providing sufficient potency in order to ameliorate or treat the cancer affecting the subject while avoiding serious side effects. A safe and effective amount will vary depending on the age of the subject, the physical condition of the subject being treated, the severity of the disease, the duration of treatment and the nature of any concurrent therapy, and its determination is within the skill of the ordinary physician.

A therapeutically active amount of a pharmaceutical composition of the present invention means an amount effective, at dosages and for periods of time necessary to achieve the desired result. This may also vary according to factors such as the disease state, age, sex, and weight of the subject and the ability of the hepoxilin analog to elicit a desired response in the subject. A dosage of around 4 mg/kg is likely a suitable initial dosage for a mammal and this dosage may be adjusted as required to provide a safe and effective amount. Dosage regima may be adjusted to provide the optimum therapeutic response. For example, several divided doses may be administered daily or the dose may be proportionally reduced as indicated by the exigencies of the therapeutic situation.

By pharmaceutically acceptable carrier as used herein is meant one or more compatible solid or liquid delivery systems. Some examples include but are not limited to starches, sugars, cellulose and its derivatives, powdered tragacanth, malt, gelatin, collagen, talc, stearic acids, magnesium stearate, calcium sulfate, vegetable oils, polyols, agar, alginic acids, pyrogen free water, isotonic saline, phosphate buffer, and other suitable non-toxic substances used in pharmaceutical formulations. Other excipients such as wetting agents and lubricants, tableting agents, stabilizers, anti-oxidants and preservatives are also contemplated.

The compositions described herein can be prepared by known methods for the preparation of pharmaceutically acceptable compositions which can be administered to subjects, such that an effective quantity of the hepoxilin analog or analogs is combined in a mixture with a pharmaceutically acceptable carrier. Suitable carriers are described for example in Remington's Pharmaceutical Sciences (Mack Publishing Company, Easton, Pa., USA, 1985). On this basis the compositions include, albeit not exclusively, solutions of the hepoxilin analog(s) in association with one or more pharmaceutically acceptable vehicles or diluents, and contained in buffered solutions with a suitable pH and iso-osmotic with the physiological fluids.

EXAMPLES

The examples are described for the purposes of illustration and are not intended to limit the scope of the invention.

Methods of chemistry, molecular biology, protein and peptide biochemistry and immunology referred to but not explicitly described in this disclosure and examples are reported in the scientific literature and are well known to those skilled in the art.

Methods

Materials

Agents. RPMI 1640, fetal bovine serum (FBS), antibiotics (penicillin and streptomycin), phosphate-buffered saline, trypan blue and trypsin-ethylenediamine tetraacetic acid (trypsin-EDTA) were purchased from Wisent Inc. (St. Bruno, Quebec). [Methyl-$^3$H]-thymidine (25 Ci/mmol), anti-rabbit and anti-mouse IgG, horseradish peroxidase linked whole antibody, ECL western blotting detection reagents were purchased from Amersham Life Sciences (Baie d'Urfe, Quebec). Dimethylsulfoxide (DMSO) was purchased from Caledon (Georgetown, Ontario). Hepoxilin (PBT-3) was prepared in our laboratory by total chemical synthesis as previously described (Demin et al., 1993). I-BOP [1S-[1α,2α(Z),3β(1E,3S*), 4α]]-7-[3-[3-hydroxy-4-(iodophenoxy)-1-butenyl]-7-oxabicyclo[2.2.1]hept-2-yl]-5-heptenoic acid was purchased from Cayman Chemical (Ann Arbor, Mich.);. STI571 (Gleevec) from Novartis Pharma. DNeasy tissue kit was from Qiagen (Mississauga, Ontario). Prestained SDS-PAGE marker broad range was from New England Biolabs (Mississauga, Ontario). Monoclonal anti-cytochrome c antibody and anti-caspase-3 antibody were purchased from Pharmingen (Mississauga, Ontario). α-tubulin and Protein A-Agarose were purchased from Santa Cruz Biotechnology (Santa Cruz, Calif.). All other chemicals and reagents were obtained from Sigma-Aldrich (Oakville, Ontario).

Cell culture. Human leukemia K562 cells, obtained from the Hematology Department of the Hospital for Sick Children, were maintained as suspension cultures in RPMI 1640 medium containing 100 U/ml penicillin G, 100 µg/ml streptomycin, 10% (v/v) fetal bovine serum in a humidified atmosphere of 5% $CO_2$ at 37° C. The ability of the cells to exclude Trypan Blue dye was used to assess cell viability.

Quantification of apoptosis and cell viability. Induction of apoptosis and loss of cell viability after treatment with PBT-3 were assessed by staining the cells with Hoechst 33342 dye. Cells treated with 1 µM I-BOP, 2.8 µM PBT-3 and 1 µM STI571 for 6 hours were harvested and washed with PBS twice. Pellets were suspended with 5 µg/ml of Hoechst 33342 dye for 10 minutes at room temperature. Micrographs of the DNA-stained cells were taken with a Zeiss Axiovert 100 TV video camera. Images were captured using Axiovision version 3.0.6 and processed using Photoshop 5.0. Apoptotic cells were identified based on nuclear fragmentation and chromatin condensation around the nucleus.

Analysis of DNA fragmentation by gel electrophoresis. At desired times after I-BOP, PBT-3 and STI571 treatment, $2\times10^6$ cells were washed twice with PBS, and DNA was extracted with DNeasy tissue kit from. The samples were loaded on 2% agarose gel containing ethidium bromide (0.2 µg/ml). DNA fragments of known size were used as a reference marker. After electrophoresis at 25 V for 5 hours, the gels were photographed under trans-UV illumination.

Western blot. Serum-starved cells were treated with I-BOP, STI571 with or without 2.8 µM PBT-3 for 24 hours. Treatment was terminated by washing cells with ice-cold PBS buffer. Cell lysates were prepared in buffer containing 20 mM Tris-HCl pH 7.4, 150 mM NaCl, 1 mM EDTA, 1 mM EGTA, 1% Triton X-100, 2.5 mM sodium pyrophosphate, 1 mM β-glycerophosphate, 1 mM sodium orthovanadate, 1 mM PMSF and 1 µM leupeptin on ice for 60 minutes. The lysates were clarified by centrifugation at 15,000×g for 15 minutes at 4° C. Lysates were subjected to protein assay and kept at −80° C. 250 µg protein was immunoprecipitated with anti-cytochrome c antibody or anti-caspase-3 antibody coupled to protein A-agarose beads. After washing of the immunocomplexes with lysis buffer, SDS-PAGE sample loading buffer was added and the mixture was boiled for 5 minutes. After centrifugation, the supernatant was loaded onto 10-12% SDS-PAGE gel, and transferred to the Trans-Blot Nitrocellulose membrane (Bio-Rad). Protein bands on the nitrocellulose membranes were checked visually with Ponceau S-staining to assure equivalent protein loading/transfer comparing different samples. Membranes were blocked with nonfat dry milk (5%, w/v) in PBS containing 0.5% (v/v) Tween-20 for one hour at room temperature and then incubated with 1:1000 dilution of anti-cytochrome c and anti-caspase-3 antibodies overnight at 4° C.; secondary antibody of horseradish peroxidase anti-rabbit or anti-mouse antibody was used at 1:2000 dilution. Bound antibodies were detected using enhanced chemilluminescence (ECL) kit and the membranes were exposed to Hyperfilm for ECL.

Statistical analysis. The observed differences in thymidine incorporation were analyzed using an unpaired double-factor analysis of variance test on StatView (Macintosh).

Thymidine Incorporation

Cells were seeded in 24 well dishes at a cell number of $5\times10^4$ cells/ml in starving medium (SM) of alpha Modified Eagle's Medium without fetal bovine serum (FBS) supplementation and incubated at 37° C. for 12 h. Tritiated thymidine ([$^3$H]-Thymidine; 25 Ci/mmol stock) was diluted in SM to a final activity of 25 mCi/mmol. The pharmacological agents tested were all diluted from their respective stocks to the desired concentration(s) with the tritiated SM. Cells receiving no drug treatments and cells treated with DMSO only were used as controls. SM was removed from the dishes, then treated with the various pharmacological agents in SM containing tritiated thymidine for 6 h at 37° C. PBT-3 was used at 2.8 µM in DMSO, (other than in dose response studies), I-BOP was used at 1.0 µM (in DMSO) and U46619 was used at 1.0 µM (in DMSO). Cells were trypsinized after 6 h and washed through Whatman GF-B/C membranes along with the supernatant. Dried membranes were deposited in scintillation vials with 8ml scintillation cocktail and the radioactivity present in the cells was counted with a liquid scintillation counter.

Cell Lysate Preparation for Akt Expression

Cells were seeded in 100 mm culture dishes at a cell count of $5\times10^4$ cells/ml in 10 ml of SM and incubated at 37° C. for 12 h. Drug treatments were: DMSO as control, 0.05 µM I-BOP in DMSO, 0.5 µM I-BOP with 2.8 µM PBT-3, or 2.8 µM PBT-3 in DMSO. These concentrations were chosen based on results generated from the cell proliferation studies using thymidine incorporation. Cells were treated with drugs as described above for 6 h. After 6 h, cells were washed with 1×PBS and scraped, pelleted by centrifugation (1500 rpm, 5 min, room temperature), and washed again and pelleted as above. 200 µl cell lysis buffer (20 mM Tris-d pH 7.4, 150 mM NaCl, 1 mM EDTA, 1 mM EGTA, 1% Tx-100, 2.5 mM $Na_4P_2O_7$, 1 mM β-glycerophosphate, 1 mM $Na_3PO_4$, 1 µg/ml leupeptin, and 1 mM PMSF) were added to resuspend each pellet followed by 30 minutes of incubation on ice. Then the cell lysates were sonicated for 10 seconds. 20 min incubation on ice was followed by centrifugation at 13,000 g at 4° C. for 15 min. Protein concentration was determined using a BSA standard with a BCA protein assay kit, prior to Western blotting.

Western Blotting

Aliquots of protein (40 µg) were heated to 90° C. in SDS sample load buffer for 5 minutes, then separated by SDS-PAGE on 10% gels and transferred to nitrocellulose membranes. Membranes were stained with Ponceau stain (Sigma) to ensure homogeneous transfer of proteins to the membranes and to allow for accurate marking of the transferred prestained marker (Biorad) for estimation of protein molecular weights. Ponceau-stained membranes were washed 3× in TBS-T (0.05% Tween 20 in 1× Tris-buffered saline) and were blocked with 5% non-fat dry milk in TBS-T for 1 h at room temperature. Blocked membranes were incubated with Akt (1:2500), pAkt (1:2500) or Bcl-XL (1:2000) antibodies in 1% BSA-TBS-T at room temperature for 90 min. Membranes were then washed 5× in TBS-T. Bound first antibodies were detected by HRP-anti-rabbit immunoglobulins at 1:1000 in 5% non-fat dry milk for 1 h at room temperature, washing 5× in TBS-T then with enhanced chemiluminscent autoradiography (ECL). Membranes were stripped and reblocked then incubated with α-tubulin antibody (1:1000) as a loading control for the same amount of protein. Anti-mouse-HRP immunoglobulins were used to detect α-tubulin binding.

FACS

Cells were seeded at $1 \times 10^6$ cells/ml and treated as above. Cells were scraped into 1×PBS, pelleted, washed, and repelleted as above. Cells were washed with PBS twice and scraped. The cells were pelleted by centrifugation at 1500 rpm, 5 min, at 23° C. and washed again. Cells were fixed with 50 µl PBS/HBSS with 2% calf serum and then with addition of 1 ml ice cold 80% ethanol. Samples were incubated on ice for 30 min and PBS/HBSS fixing was repeated and followed by adding 1 ml 70% ethanol. Centrifugation (1500 rpm, 5 min, room temperature) was performed to produce cell pellets that were resuspended by 250 µl of 0.1 mg/ml Propidium Iodide (Sigma) with 0.6% NP-40. 250 µl of 2 mg/ml RNAse was added and mixed well. Cells were incubated in the dark for 30 min at room temperature. Samples were then filtered through 85 µm Nitex mesh and the stained cells were analyzed on a flow cytometer of FACScan (Becton-Dickinson). The acquisition was done with 10,000 events per sample. The CellQuest (Becton-Dickinson) statistic analysis was performed in each individual experiment.

Example 1

The effect of hepoxilin analogs on leukemia cells was examined using the CML K562 cell line. This cell line was derived from a human CML patient and is an accepted model of human chronic leukemia. The K562 cell line expresses the bcr/abl protein (Lozzio & Lozzio, 1975). It is relatively resistant to apoptosis (Martin et al., 1990), but ST1571 and other agents appear to control cell growth for a while before the cells overcome the drug effect (Weisberg & Griffin, 2000).

The effect of various doses of the hepoxilin analog PBT-3 on growth of K562 cells was first examined. As seen in FIG. 1, PBT-3 inhibited growth of K562 cells, as measured by $^3$H thymidine incorporation, with a maximum effect at 1 µg/ml PBT-3.

Figure 2:
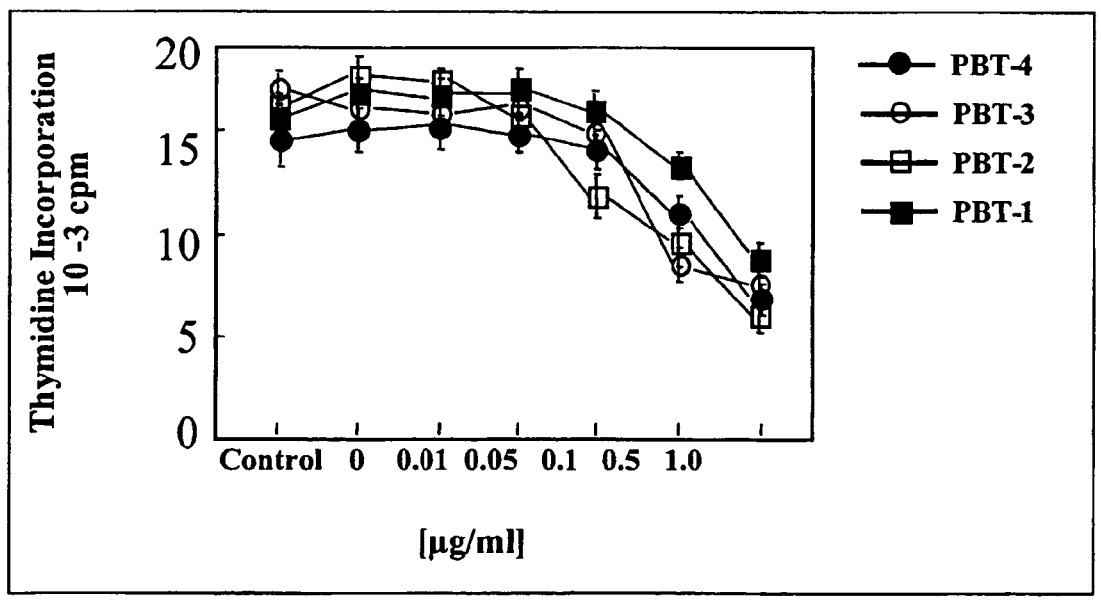
FIG. 2 shows the effect of various doses of PBT-1, PBT-2, PBT-3 and PBT-4 on $^3$H-thymidine incorporation in K562 CML cells.

FIG. 2 shows that all four analogs examined, PBT-1, PBT-2, PBT-3 and PBT-4, gave similar dose response effects in inhibiting K562 cell growth.

Figure 3:
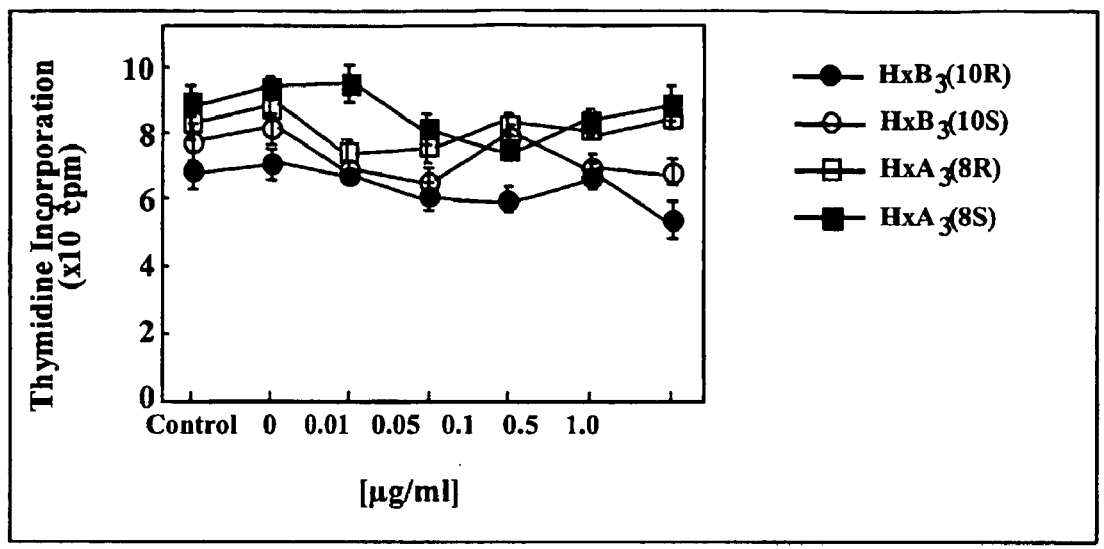
FIG. 3 shows the effect of four native hepoxilins on $^3$H-thymidine incorporation in K562 CML cells.

The effect of native hepoxilins was also examined. FIG. 3 shows that native hepoxilins did not inhibit K562 cell growth, probably due to poorer stability than the PBT analogs.

Figure 4:
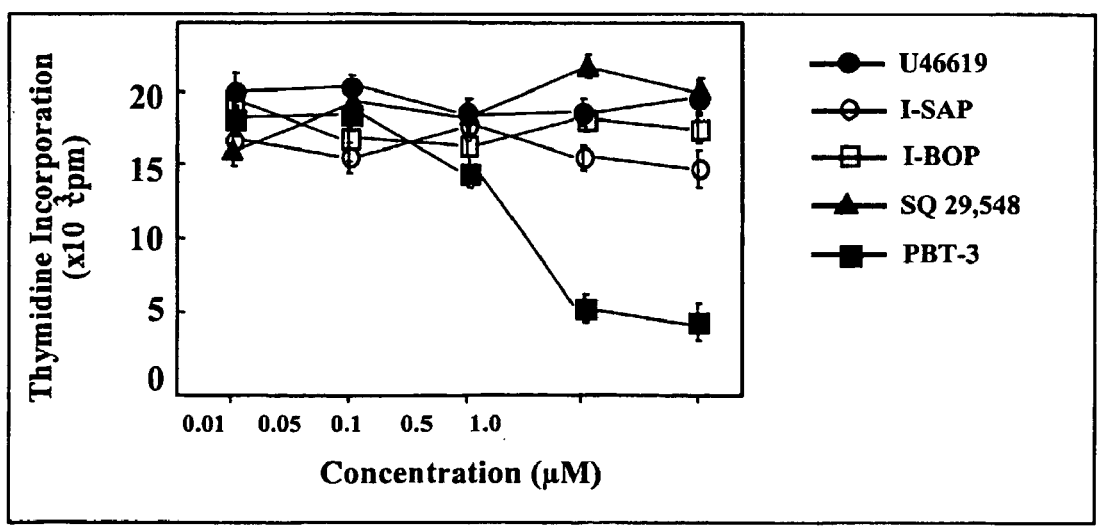
FIG. 4 shows the effect of PBT-3, the thromboxane receptor agonists, I-BOP, I-SAP and U46619 and the thromboxane receptor antagonist SP29,548 on $^3$H-thymidine incorporation in K562 CML cells.

The effect of the thromboxane receptor agonists, I-BOP, I-SAP and U46619 and the antagonist SQ 29,548, on the growth of K562 cells was examined, in comparison to the effect of PBT-3. FIG. 4 shows that neither the thromboxane receptor agonists nor the thromboxane receptor antagonist affected K562 cell growth, suggesting that the growth of these cells is not mediated by the thromboxane pathway. The apoptotic effect of PBT-3 is therefore likely mediated by a mechanism independent of the thromboxane pathway.

Example 2

Apoptotic Effect of PBT-3 on K562 Cells

Figure 5:
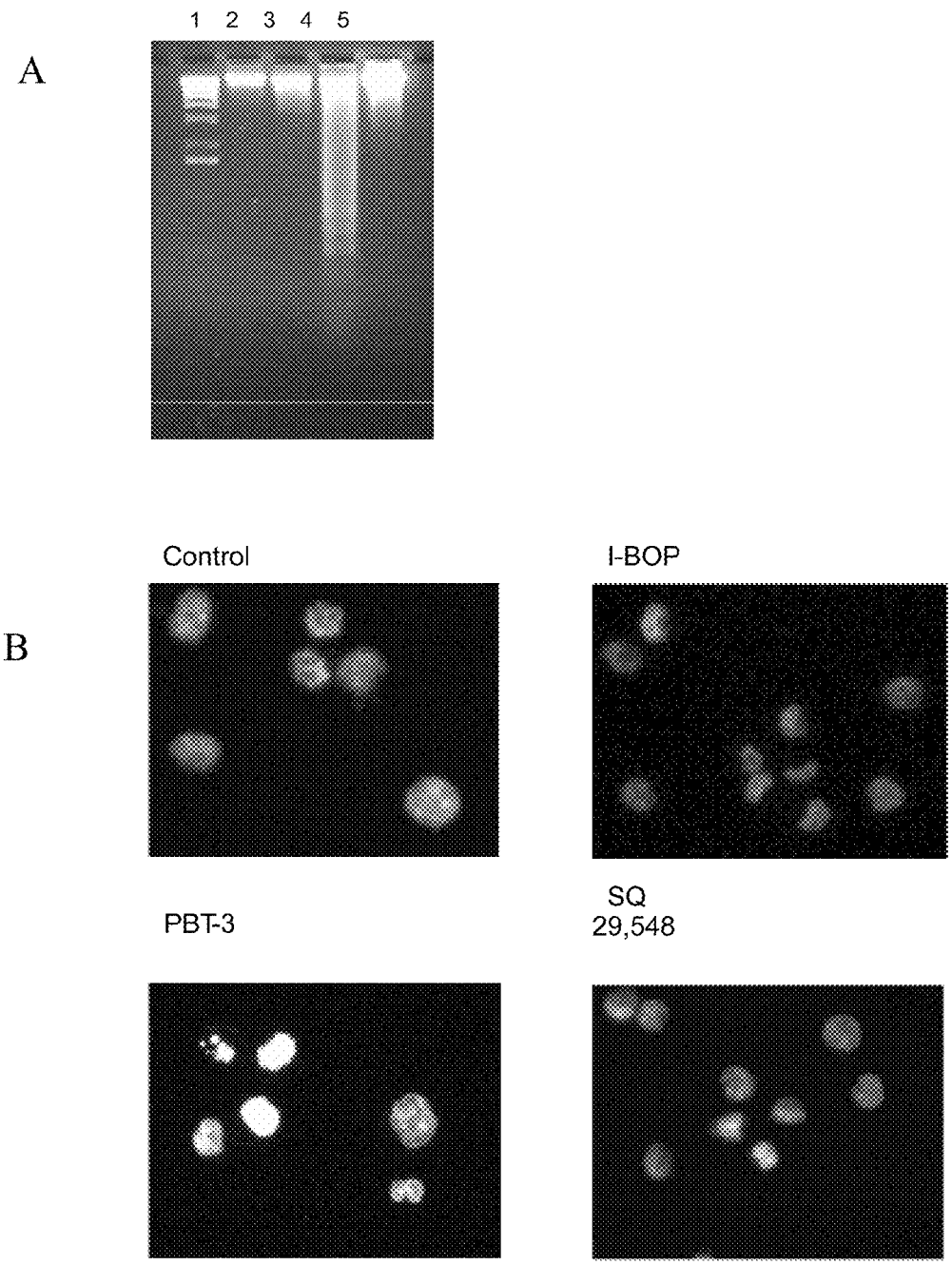
FIG. 5, Panel A, shows an agarose gel of DNA fragments. Lane 1: 1 Kb DNA marker; Lane 2: K562 cells cultured in growth medium only for 24 hours; Lane 3: K562 cells cultured with 1 µg/ml PBT-3 for 24 hours; Lane 4: K562 cells cultured with 1 µg/ml PBT-3 for 72 hours; Lane 5: K562 cells cultured in growth medium only for 72 hours.

Studies were carried out to determine if PBT-3 affected apoptosis in K562 CML cells. Cells were cultured for 24 or 72 hours in the presence of growth medium (control) or PBT-3 (2.8 µM). Apoptosis was examined by DNA laddering. Cultures were harvested, DNA was extracted with DNeasy (Qiagen) and samples were loaded on a 2% agarose gel containing 0.2 µg/ml ethidium bromide. A λ BstII DNA digest with DNA fragments of known size was used as a reference marker. After electrophoresis at 25V for 5 h, gels were photographed under trans-UV illumination. A typical gel is shown in FIG. 5, Panel A.

These results demonstrate that PBT-3 causes DNA fragmentation associated with apoptosis within a 24 hour to 72 hour period.

Nuclear fragmentation was assessed by direct microscopy of treated cells stained with Hoechst 33342 dye. After culture with PBT-3, I—BOP or STI571, cells were suspended with 5 µg/ml of dye for 10 min. at 23° C.; then washed with growth medium and micrographs taken. As seen in FIG. 5, Panel B, treatment with PBT-3 produced apoptotic cells, which show fragmentation of the nucleus and chromatin condensation around the nucleus.

No similar apoptotic effect was seen in cells treated with STI571 (1 µM) or the 1 µm thromboxane receptor agonist, I—BOP, indicating that the apoptotic effect of the hepoxilin analogs is not mediated through its previously demonstrated effects on the thromboxane pathway.

Figure 6:
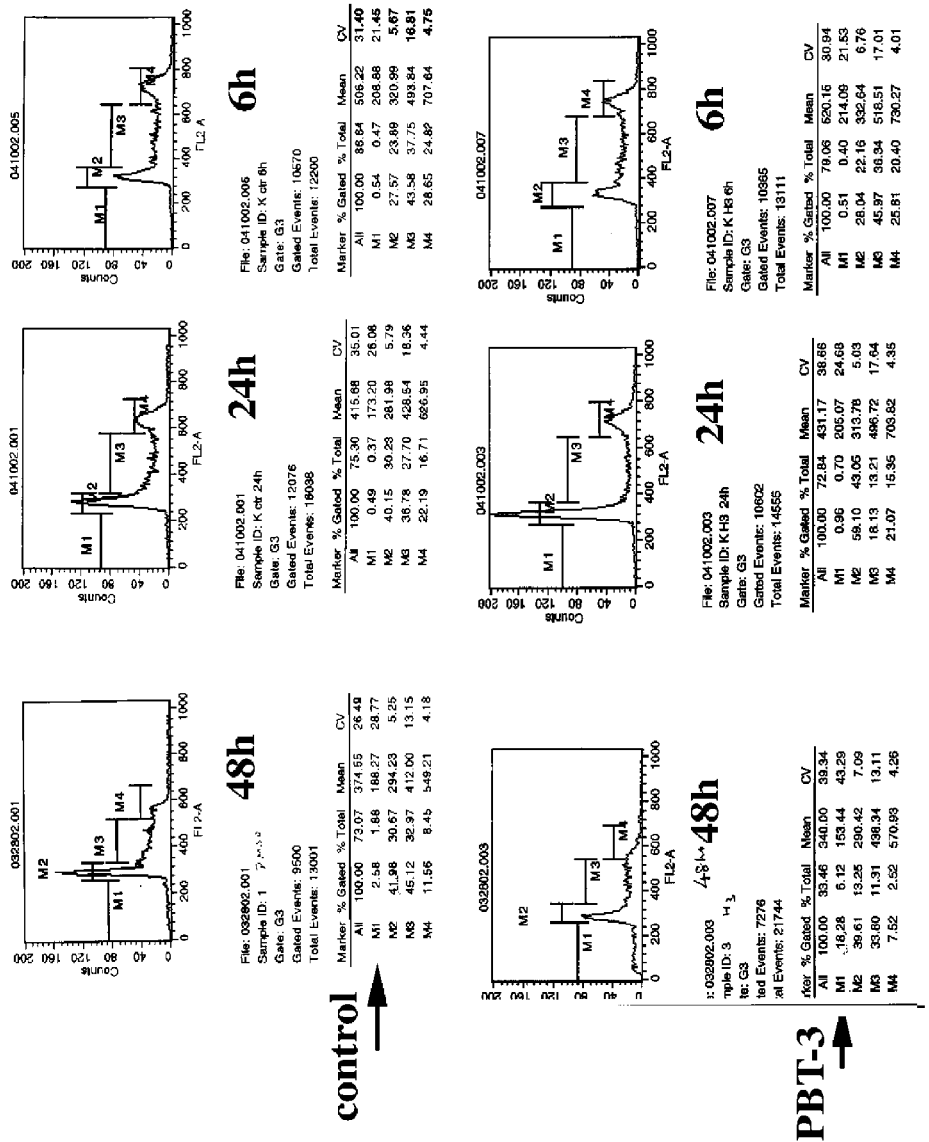
FIG. 6 shows a FACS analysis of the time course of the apoptotic effect of PBT-3 on K562 CML cells.

FIG. 6 shows the time course of the apoptotic effect of 1 µg/ml PBT-3 on K562 cells by FACS analysis.

Figure 7:
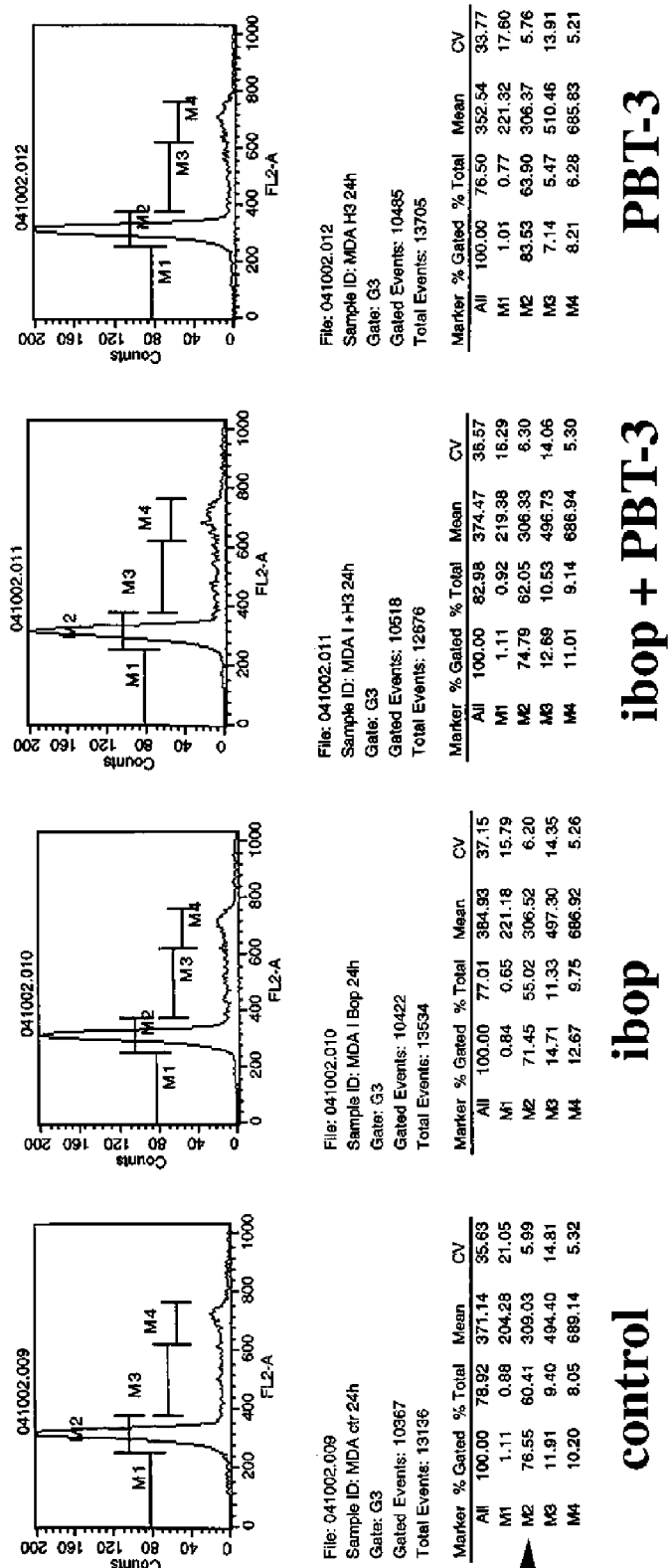
FIG. 7 shows a FACS analysis of the synchronisation of the breast cancer cell line, MDA-MB 231, to Go phase by PBT-3.

FIG. 7 shows the synchronisation effect of PBT-3 on breast cancer cells, MDA-MB 231.

Figure 8:
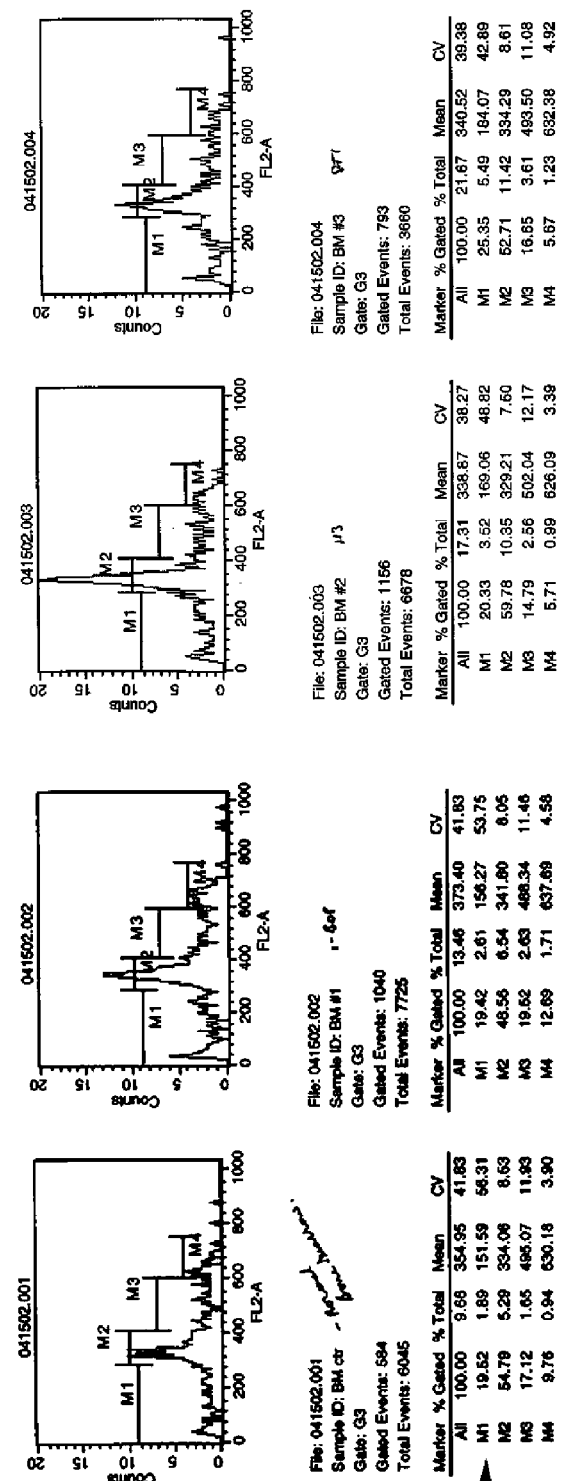
FIG. 8 shows the lack of apoptotic effect of PBT-3 on the growth of normal bone marrow cells.
Figure 9:
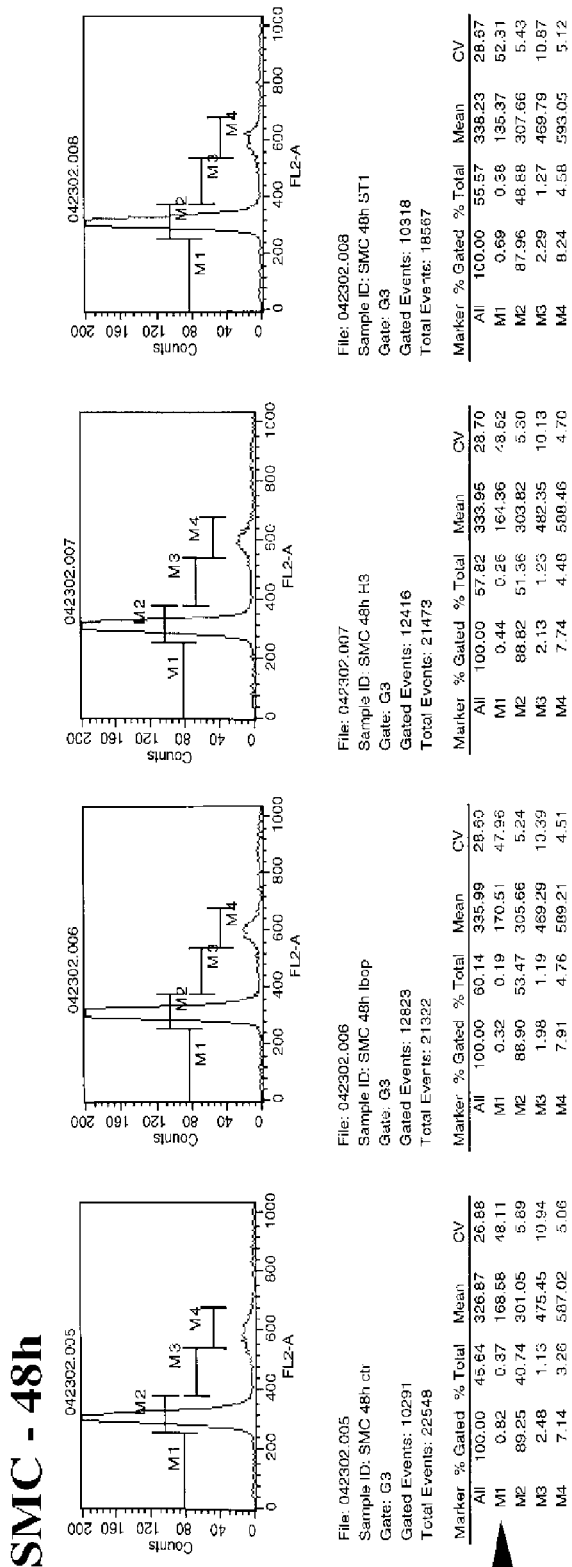
FIG. 9 shows the lack of apoptotic effect of PBT-3 on the growth of normal smooth muscle cells.
Figure 10:
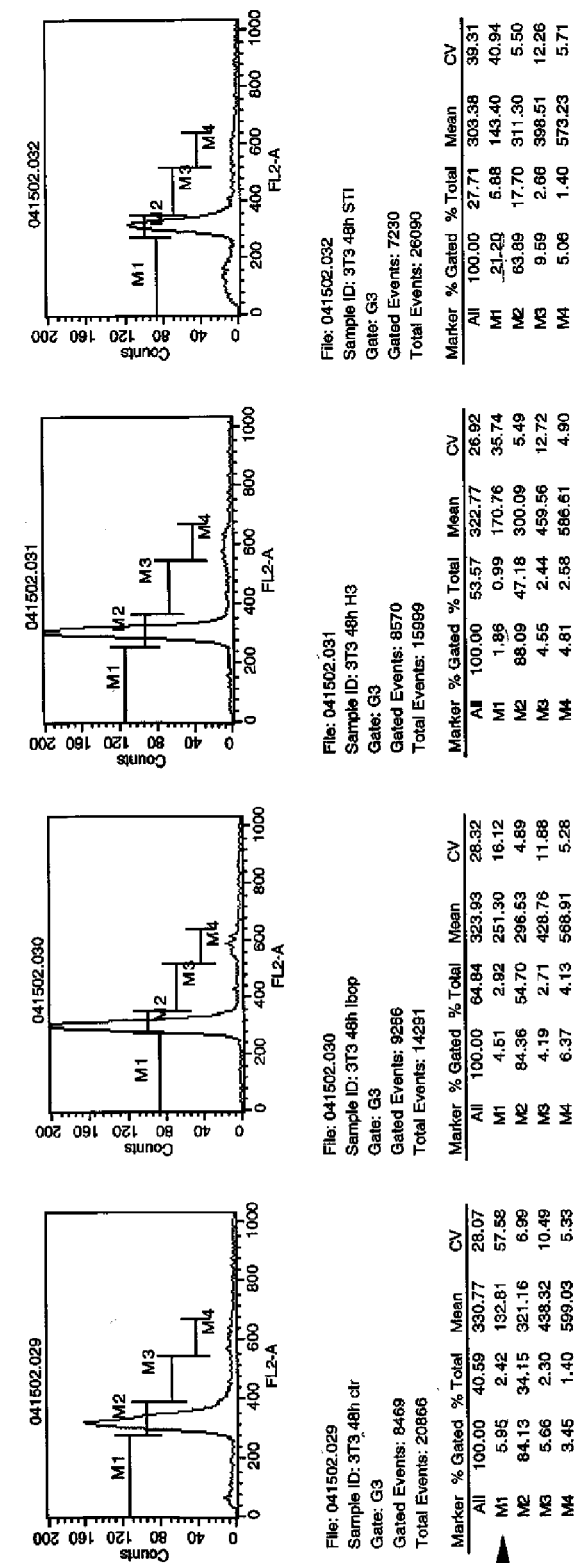
FIG. 10 shows the lack of apoptotic effect of PBT-3 on the growth of 3T3 L1 adipocytes.

FIGS. 8, 9 and 10 show the results of a FACS analysis demonstrating that PBT-3 has no apoptotic effect on normal bone marrow cells, normal aortic smooth muscle cells and normal (3T3 L1) adipocytes.

Example 3

Effect of PBT-3 on Akt Expression

The effect of PBT-3 on Akt expression in K562 cells was examined as described above.

Figure 11:
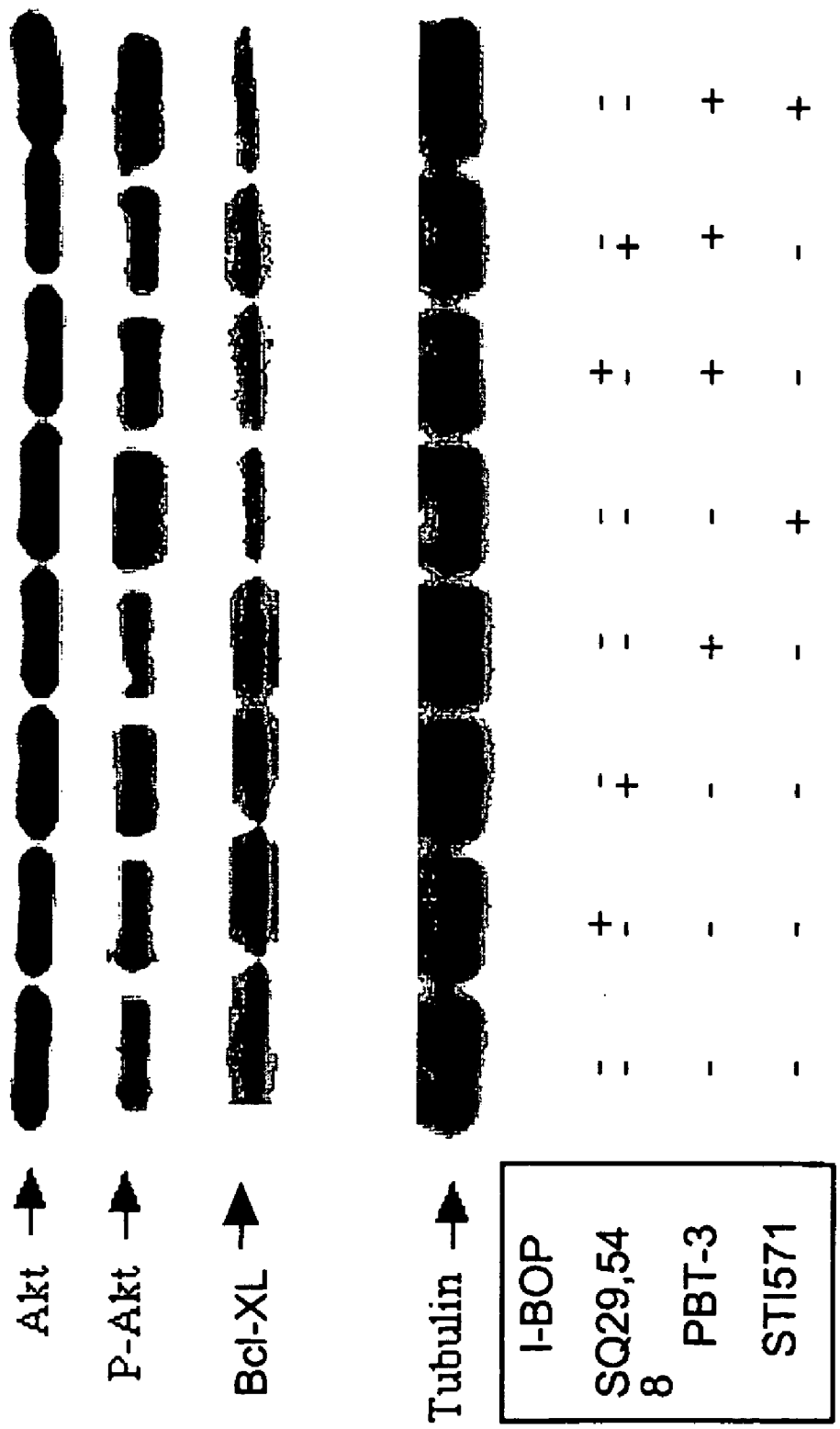
FIG. 11 shows a Western blot of Akt and Phospho-Akt proteins derived from K562 CML cells after treatment in culture with the indicated combinations of the compounds, I—BOP, SQ29548 and PBT-3.

FIG. 11 shows a Western blot showing that STI-571 blocked the expression of the Bcl pathway (Bcl-XL), while PBT-3 was essentially inactive on this pathway. On the other hand, PBT-3 blocked phosphorylation of Akt, while STI-571 increased it. These results suggest that both compounds (PBT-3 and STI-571) may be useful as complementary medicines to block expression of the two separate pathways (Akt and Bcl) in leukemia.

Example 4

Figure 12:
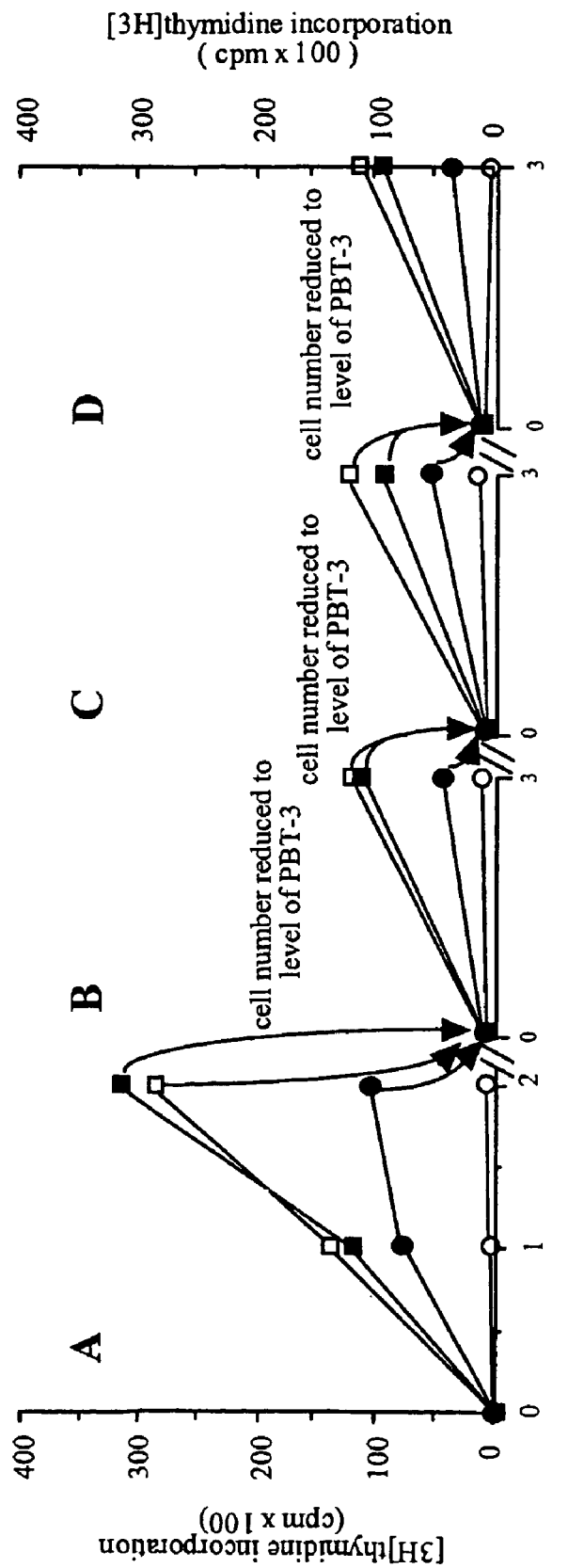
FIG. 12, Panel A, shows $^3$H thymidine uptake in K562 cells untreated (□), or treated with DMSO (■), 28 µM PBT-3 in DMSO (○) or 1 µM STI571 in DMSO (●) for 2 days; Panel B shows $^3$H thymidine uptake in the same treatment groups of cells after washout of drugs, where cell number was reduced to that observed in Panel A after PBT-3 treatment and incubation continued in the absence of drugs for 3 days in 10% FBS; Panels C and D show $^3$H thymidine uptake in the same groups of cells subjected to two further cell reductions and incubations in the absence of drugs as in Panel B.

K562 cells ($3 \times 10^5$ cells/plate) were cultured for 2 days in 1% FBS/αMEM in the presence of 28 µM PBT-3 (○) or 1 µM STI (●) and $^3$H thymidine incorporation was determined. Untreated control cells (□) and cells treated with DMSO alone (■) were also examined (test compounds were dissolved in DMSO). Results are shown in FIG. 12, Panel A. The cell number in all dishes was reduced to that observed after two days of PBT-3 treatment (7.5×10³/ml) and the cells were subsequently cultured for 3 days in 10% FBS in the absence of the test compounds. The results are shown in FIG. 12, Panel B. A similar cell reduction and three day culture was repeated twice and the results are shown in FIG. 12, Panels C and D. These results show the extent of recovery of the cells after treatment and washout of drug, and the extent of cell kill on exposure to PBT-3.

Figure 13:
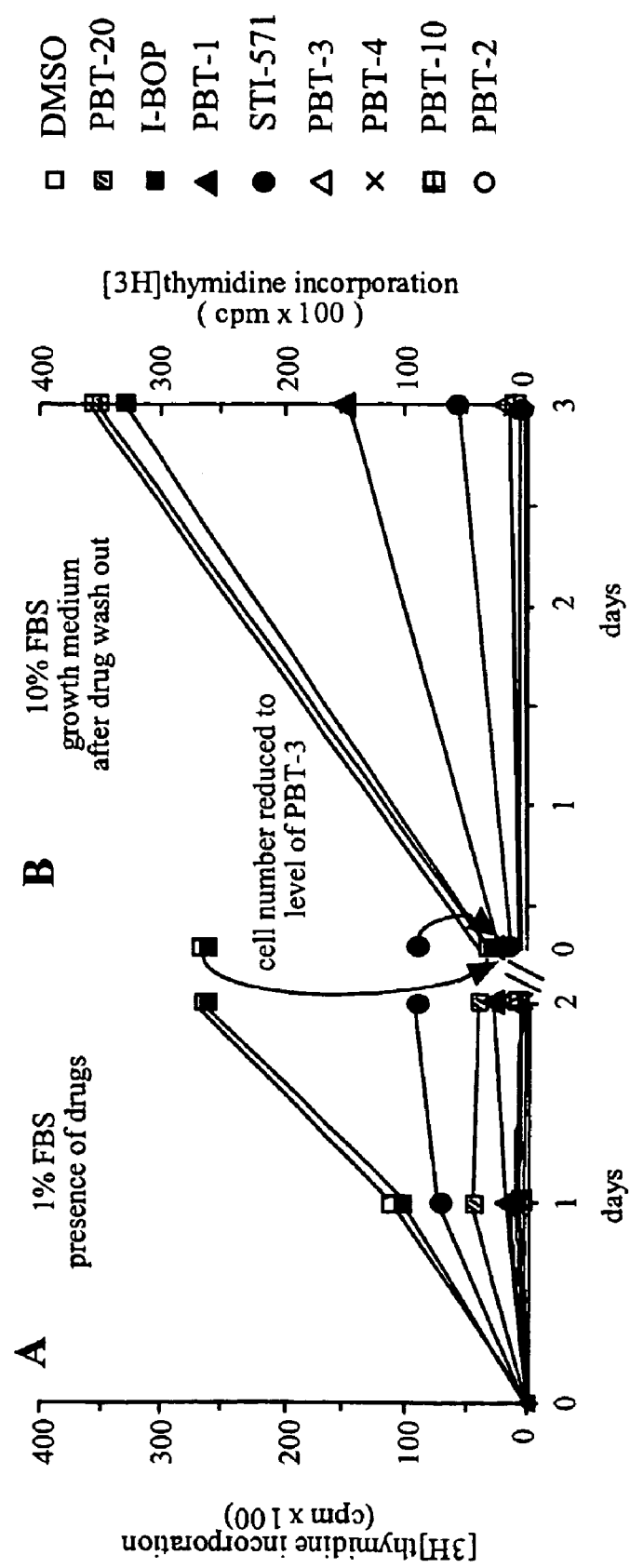
FIG. 13, Panel A, shows $^3$H thymidine uptake in K562 cells treated with the indicated compound for 2 days; Panel B shows $^3$H thymidine uptake in the same treatment groups of cells, where cell number was reduced to that observed in Panel A after PBT-3 treatment and incubation continued for 3 days in 10% FBS.

A similar study was carried out in which K562 cells were treated with DMSO (□), PBT-20 (▨), I—BOP (■), PBT-1 (▲), STI571 (●), PBT-3 (Δ), PBT-4 (X), PBT-10 (⊞) or PBT-2 (○) for the same time period, followed by cell number reduction and culture in the absence of test compounds for 3 days (I—BOP and STI571 at 1 µM and all PBT analogues at 28 µM). Results are shown in FIG. 13. Effectiveness of the various treatments in inhibiting cell growth was in the order in which the treatments are listed in the panel to the right of the graph, PBT-2 being the most effective treatment. The hepoxilin analogs compare very favourably in efficacy with STI571.

Example 5

Figure 14:
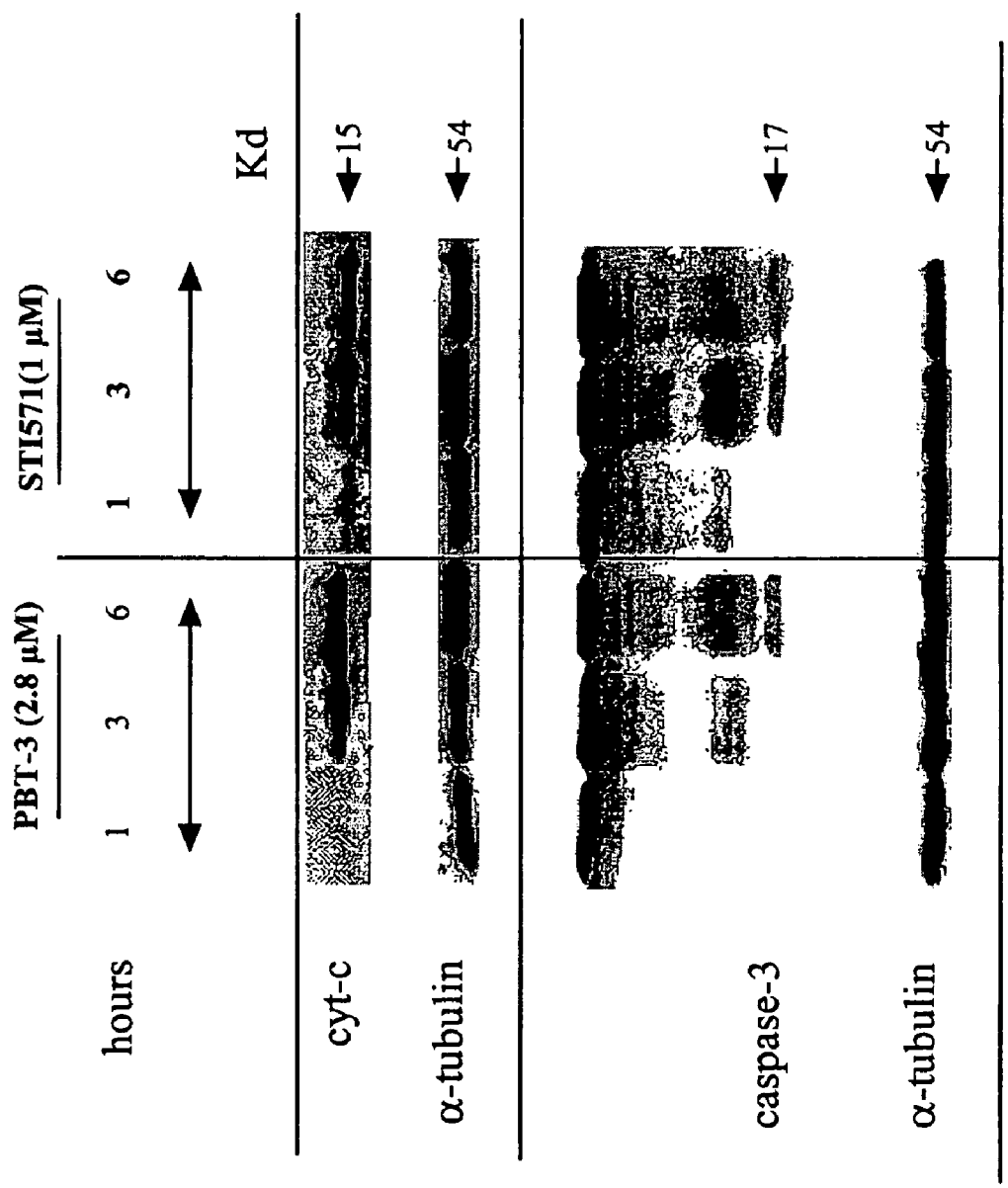
FIG. 14 shows a Western blot of time-dependent enhanced release of cytosolic cytochrome c by PBT-3 and STI571 and degradation of caspase-3 to a 17 kD fragment.

In order to determine whether PBT-3 could overcome the anti-apoptotic effect of BCR-ABL on the mitochondria, the effect of PBT-3 on cytochrome c release was studied. FIG. 14 shows that both PBT-3 and STI571 caused release of cytochrome c into the cytoplasm within 3 hours. Caspase-3 was activated, as evidenced by its cleavage into a 17 kDa fragment. PBT3-induced caspase-3 activation was delayed to 6 hr, compared to 3 hr by STI571.

The present invention is not limited to the features of the embodiments described herein, but includes all variations and modifications within the scope of the claims.

REFERENCES

Cheng G-S (2000) Dramatic results in Trial of new leukemic drug. *Family Practice News.*
Cherath L (1995) Chronic leukemia. *The Gale Encyclopedia of Medicine.*
Demin P M and Pace-Asciak C R (1993) Synthesis of racemic 11,12-cyclopropyl analogs of hepoxilins A₃ and B₃. *Tetrahedron Lett.* 34: 4305-4308.
Jankov et al. (2002), J.P.E.T., v. 301, pp. 435-440
Laneuville O, Reynaud D, Grinstein S, Nigam S and Pace-Asciak C R (1993) Hepoxilin A₃ inhibits the rise in free intracellular calcium evoked by formyl-methionyl-leucyl-phenylalanine, platelet activating factor and leukotriene B₄. *Biochem. J.* 295: 393-397.
Lim D and Muir J (2001) Imatinib for chronic myelogenous leukemia: a NICE mess. *Lancet* 358: 1903.
Lozzio C B and Lozzio B B (1975) Human chorionic myelogenous leukemia cell line with positive philadelphia chromosome. *Blood.* 45: 321.
Martin S, Lennon S, Bonham A and Cotter T (1990) Induction of apoptosis (programmed cell death) in human leukemia cells by inhibitors of RNA or protein synthesis. *J. Immunol.* 145: 1859.
Mauro M J, O'Dwyer M, Heinrich M C and Drucker B J (2002) STI571: A paradigm of new agents for cancer therapeutics. *J. Clin. Oncol.* 20: 325-334.
McWhirter J R and Wang J Y K (1991) Activation of tyrosine kinase and microfilament-binding function od c-abl by bcr sequences in bcr/abl fusion proteins. *Mol. Cell Biol.* 11: 1553.
O'Brien S G (2001) Imatinib for chronic myelogenous leukemia: a NICE mess. *Lancet:* 1902-3.
Pace-Asciak C R and Martin J M (1984) Hepoxilin, a new family of insulin secretagogues formed by intact rat pancreatic islets. *Prostagl. Leukotriene and Med.* 16: 173-180.
Pace-Asciak C R, Reynaud D, Demin P and Nigam S (1999) The hepoxilins. A review. In: *Lipoxygenases and Their Metabolites—Biological Functions. Advances in Experimental Medicine and Biology, Vol:* 447, Eds. S. Nigam and C. R. Pace-Asciak, Kluwer Academic/Plenum Publishers, New York, pp. 123-132.
Rajaratnam G and Edwards J (2001) Imatinib for chronic myelogenous leukemia: a NICE mess. *Lancet* 358: 1902.
Seppa N (2001) Leukemia overpowers drug in two ways, (STI-571 and chronic myelogenous leukemia). *Science News.*
Tran M (1995) Leukemia. *Gale Encyclopedia of Alternative Medicine.*
Weisberg E and Griffin J D (2000) Mechanism of resistance to the ABL tyrosine kinase inhibitor STI571 in BCR/ABL-transformed hematopoietic cell lines. *Blood.* 95: 3498-3505.

I claim:

1. A method for treating a cancer in a mammal comprising administering to the mammal an effective amount of at least one hepoxilin analog of the formula:

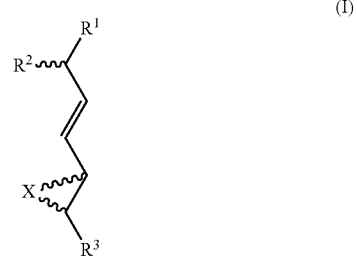

(I)

wherein X is S, NH or CH₂
$R^1$ is lower alkyl;
—CH₂CH═CH—(CH₂)₃—COR" wherein R" is OH, O— lower alkyl or alkenyl; or
Y—$R^4$ wherein
Y is —CH₂—CH═CH—(CH₂)₃, lower alkyl or alkenyl and
$R^4$ is CONH-Z or COO-Z wherein
Z is a sugar moiety;
$R^2$ is OH, NH₂, SH, OPO₃H, lower alkyl or alkenyl or O— lower alkyl or alkenyl; and
$R^3$ is lower alkenyl or —CH₂—CH═CH—(CH₂)₄—R'"
wherein R" is CH₃, CH₂OH, CH₂ —O— lower alkyl or alkenyl, phenyl or substituted phenyl or

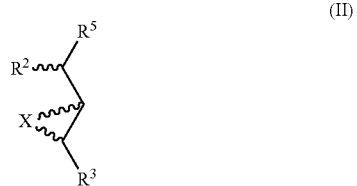

(II)

wherein X, $R_2$ and $R_3$ are as defined for formula I and
$R^5$ is lower alkenyl;
—CH═CH—CH₂—CH═CH—(CH₂)₃—COR"
wherein R"═OH or O— lower alkyl or alkenyl; or Y—R⁶ wherein
Y is —CH=CH—CH₂—CH=CH—(CH₂)₃, lower alkyl or alkenyl and
R⁶ is CONH-Z or COO-Z wherein
Z is a sugar moiety,
wherein the cancer is selected from the group consisting of leukemia and cancer of the prostate or breast.

2. The method of claim 1 wherein the at least one hepoxilin analog is selected from the group consisting of:
(a) 8(S)-hydroxy-11,12-cyclopropyl-eicosa-5Z,9E,14Z-trienoic acid methyl ester;
(b) 8(R)-hydroxy-11,12-cyclopropyl-eicosa-5Z,E,14Z-trienoic acid methyl ester;
(c) 10(S)-hydroxy-11,12-cyclopropyl-eicosa-5Z,8Z,14Z-trienoic acid methyl ester;
(d) 10(R)-hydroxy-11,12-cyclopropyl-eicosa-5Z,8Z,14Z-trienoic acid methyl ester;
(e) 1-(2-deoxy-2-amidogalactopyranosyl)-8(S)-hydroxy-11,12-cyclopropyl-eicosa-5Z,9E,14Z-trienamide;
(f) 1-(2-deoxy-2-amidogalactopyranosyl)-8(R)-hydroxy-11,12-cyclopropyl-eicosa-5Z,9E,14Z-trienamide;
(g) 1-(2-deoxy-2-amidogalactopyranosyl)-10(S)-hydroxy-11,12-cyclopropyl-eicosa-5Z,8Z,14Z-trienamide;
(h) 1-(2-deoxy-2-amidogalactopyranosyl)-10(R)-hydroxy-11,12-cyclopropyl-eicosa-5Z,8Z,14Z-trienamide;
(i) 1-(6-galactopyranosyl)-8(S)-hydroxy-11,12-cyclopropyl-eicosa-5Z,9E,14Z-trienoate;
(j) 1-(6-galactopyranosyl)-8(R)-hydroxy-11,12-cyclopropyl-eicosa-5Z,9E,14Z-trienoate;
(k) 1-(6-galactopyranosyl)-10(S)-hydroxy-11,12-cyclopropyl-eicosa-5Z,8Z,14Z-trienoate;
(l) 1-(6-galactopyranosyl)-10(R)-hydroxy-11,12-cyclopropyl-eicosa-5Z,8Z,14Z-trienoate;
(m) 8(S)-hydroxy-11,12-cyclopropyl-eicosa-5Z,9E,14Z-trienoic acid;
(n) 8(R)-hydroxy-11,12-cyclopropyl-eicosa-5Z,9E,14Z-trienoic acid;
(o) 10(S)-hydroxy-11,12-cyclopropyl-eicosa-5Z,8Z,14Z-trienoic acid; and
(p) 10(R)-hydroxy-11,12-cyclopropyl-eicosa-5Z,8Z,14Z-trienoic acid.

3. The method of claim 1 wherein the at least one hepoxilin analog is 10(S)-hydroxy-11,12-cyclopropyl-eicosa-5Z,8Z,14Z-trienoic acid methyl ester.

4. The method of claim 1 wherein at least one additional anti-cancer drug is administered to the mammal.

5. The method of claim 4 wherein the additional anti-cancer drug is imatinib mesylate.

6. The method of claim 1 wherein the cancer is an acute or chronic leukemia.

7. The method of claim 6 wherein the leukemia is chronic myelogenous leukemia.

8. The method of claim 7 wherein the mammal is a human.

9. A method for promoting apoptosis or restoring normal apoptosis in a cancer cell comprising administering to the cell an effective amount of at least one hepoxilin analog of the formula:

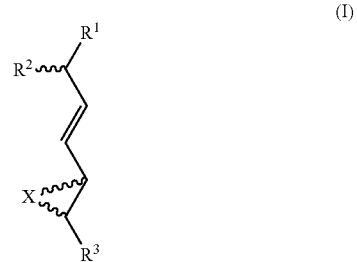

(I)

wherein X is S, NH or C₂
R¹ is lower alkenyl;
—CH₂CH=CH—(CH₂)₃—COR" wherein R" is OH, O— lower alkyl or alkenyl; or
Y—R⁴ wherein
Y is —CH₂—CH=CH—(CH₂)₃, lower alkyl or alkenyl and
R⁴ is CONH-Z or COO-Z wherein
Z is a sugar moiety;
R² is OH, NH₂, SH, OPO₃H, lower alkyl or alkenyl or O— lower alkyl or alkenyl; and
R³ is lower alkenyl or
—CH₂—CH=CH—(CH₂)₄—R''' wherein R''' is CH₃, CH₂OH, CH₂—O— lower alkyl or alkenyl, phenyl or substituted phenyl or

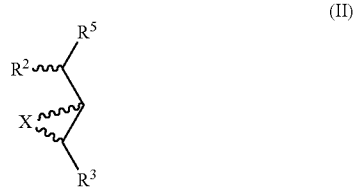

(II)

wherein X, R² and R³ are as defined for formula I and
R⁵ is lower alkenyl;
—CH=CH—CH₂—CH=CH—(CH₂)₃—COR"
wherein R"=OH or O— lower alkyl or alkenyl; or
Y—R⁶ wherein
Y is —CH=CH—CH₂—CH=CH—(CH₂)₃, lower alkyl or alkenyl and
R⁶ is CONH-Z or COO-Z wherein
Z is a sugar moiety,
wherein the cancer is selected from the group consisting of leukemia and cancer of the prostate or breast.

10. The method of claim 9 wherein the at least one hepoxilin analog is selected from the group consisting of
(a) 8(S)-hydroxy-11,12-cyclopropyl-eicosa-5Z,9E,14Z-trienoic acid methyl ester;
(b) 8(R)-hydroxy-11,12-cyclopropyl-eicosa-5Z,9E,14Z-trienoic acid methyl ester;
(c) 10(S)-hydroxy-11,12-cyclopropyl-eicosa-5Z,8Z,14Z-trienoic acid methyl ester;
(d) 10(R)-hydroxy-11,12-cyclopropyl-eicosa-5Z,8Z,14Z-trienoic acid methyl ester;
(e) 1-(2-deoxy-2-amidogalactopyranosyl)-8(S)-hydroxy-11,12-cyclopropyl-eicosa-5Z,9E,14Z-trienamide;
(f) 1-(2-deoxy-2-amidogalactopyranosyl)-8(R)-hydroxy-11,12-cyclopropyl-eicosa-5Z,9E,14Z-trienamide;

(g) 1-(2-deoxy-2-amidogalactopyranosyl)-10(S)-hydroxy-11,12-cyclopropyl-eicosa-5Z,8Z,14Z-trienamide;

(h) 1-(2-deoxy-2-amidogalactopyranosyl)-10(R)-hydroxy-11,12-cyclopropyl-eicosa-5Z,8Z,14Z-trienamide;

(i) 1-(6-galactopyranosyl)-8(S)-hydroxy-11,12-cyclopropyl-eicosa-5Z,9E,14Z-trienoate;

(j) 1-(6-galactopyranosyl)-8(R)-hydroxy-11,12-cyclopropyl-eicosa-5Z,9E,14Z-trienoate;

(k) 1-(6-galactopyranosyl)-10(S)-hydroxy-11,12-cyclopropyl-eicosa-5Z,8Z,14Z-trienoate; and (l) 1-(6-galactopyranosyl)-10(R)-hydroxy-11,12-cyclopropyl-eicosa-5Z,8Z,14Z-trienoate;

(m) 8(S)-hydroxy-11,12-cyclopropyl-eicosa-5Z,9E,14Z-trienoic acid;

(n) 8(R)-hydroxy-11,12-cyclopropyl-eicosa-5Z,9E,14Z-trienoic acid;

(o) 10(S)-hydroxy-11,12-cyclopropyl-eicosa-5Z,8Z,14Z-trienoic acid; and (p) 10(R)-hydroxy-11,12-cyclopropyl-eicosa-5Z,8Z,14Z-trienoic acid.

11. The method of claim 9 wherein the at least one hepoxilin analogue is 10(S)-hydroxy-11,12-cyclopropyl-eicosa-5Z,8Z,14Z-trienoic acid methyl ester.

12. The method of claim 9 wherein the cancer is an acute or chronic leukemia.

13. The method of claim 12 wherein the leukemia is chronic myelogenous leukemia.

14. A method of claim 1 wherein X is $CH_2$.

15. The method of claim 9 wherein X is $CH_2$.

* * * * *

UNITED STATES PATENT AND TRADEMARK OFFICE
CERTIFICATE OF CORRECTION

PATENT NO. : 7,666,905 B2
APPLICATION NO. : 10/999195
DATED : February 23, 2010
INVENTOR(S) : Cecil Pace-Asciak Page 1 of 1

It is certified that error appears in the above-identified patent and that said Letters Patent is hereby corrected as shown below:

Col. 19, Line 12, Claim 2 - "5Z,E,14Z-trienoic" should read --5Z,9E,14Z-trienoic--;

Col. 20, Line 1, Claim 9 - "wherein X is S, NH or C2" should read --wherein X is S, NH or CH2--; and Col. 22, Line 14, Claim 14 - "A method" should read --The method--.

Signed and Sealed this

Twenty-eighth Day of September, 2010

David J. Kappos
*Director of the United States Patent and Trademark Office*

UNITED STATES PATENT AND TRADEMARK OFFICE
CERTIFICATE OF CORRECTION

PATENT NO.       : 7,666,905 B2                                    Page 1 of 1
APPLICATION NO.  : 10/999195
DATED            : February 23, 2010
INVENTOR(S)      : Cecil Pace-Asciak It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 115 days.

Signed and Sealed this

Fourth Day of January, 2011

David J. Kappos
*Director of the United States Patent and Trademark Office*